United States Patent
Choi et al.

(10) Patent No.: US 7,569,639 B2
(45) Date of Patent: Aug. 4, 2009

(54) RUBBER COMPOSITION CONTAINING CYCLIC POLYSULFIDE AS VULCANIZATION AGENT AND PNEUMATIC TIRE USING THE SAME

(75) Inventors: Wonmun Choi, Hiratsuka (JP); Tomoyuki Matsumura, Hiratsuka (JP); Naoya Amino, Hiratsuka (JP); Kazuhiro Takase, Hiratsuka (JP); Daisuke Kanenari, Hiratsuka (JP); Takeshi Hotaka, Hiratsuka (JP); Junichirou Natori, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 630 days.

(21) Appl. No.: 10/545,072

(22) PCT Filed: Oct. 13, 2004

(86) PCT No.: PCT/JP2004/015451

§ 371 (c)(1),
(2), (4) Date: Aug. 9, 2005

(87) PCT Pub. No.: WO2005/035647

PCT Pub. Date: Apr. 21, 2005

(65) Prior Publication Data

US 2006/0094831 A1    May 4, 2006

(30) Foreign Application Priority Data

| Oct. 14, 2003 | (JP) | 2003-353974 |
| Oct. 24, 2003 | (JP) | 2003-364613 |
| Nov. 13, 2003 | (JP) | 2003-383808 |
| Nov. 13, 2003 | (JP) | 2003-383849 |
| Nov. 13, 2003 | (JP) | 2003-383943 |
| Nov. 14, 2003 | (JP) | 2003-385220 |
| Nov. 17, 2003 | (JP) | 2003-386800 |
| Nov. 18, 2003 | (JP) | 2003-388197 |
| Nov. 20, 2003 | (JP) | 2003-390979 |
| Nov. 27, 2003 | (JP) | 2003-397146 |

(51) Int. Cl.
C08L 81/04 (2006.01)

(52) U.S. Cl. ..................... 525/189; 525/535

(58) Field of Classification Search ............. 525/189, 525/535

See application file for complete search history.

(56) References Cited

U.S. PATENT DOCUMENTS 4,577,004 A * 3/1986 Emura et al. ............... 526/204

2002/0107338 A1 * 8/2002 Wonmun et al. ............ 525/535

FOREIGN PATENT DOCUMENTS

| JP | 58-122944 | * | 7/1983 |
| JP | 58-122944 | A | 7/1983 |
| JP | 02231202 | A | 9/1990 |
| JP | 05-051487 | A | 3/1993 |
| JP | 06-057040 | A | 3/1994 |
| JP | 10-087884 | A | 4/1998 |
| JP | 10-120788 | A | 5/1998 |
| JP | 10130442 | A | 5/1998 |
| JP | 10-151906 | A | 6/1998 |
| JP | 10-297226 | A1 | 11/1998 |
| JP | 2000-233603 | A | 8/2000 |
| JP | 2001-226528 | A | 8/2001 |
| JP | 2001-519279 | A1 | 10/2001 |
| JP | 2001-348461 | A | 12/2001 |
| JP | 2002088208 | A | 3/2002 |
| JP | 2002-105249 | A | 4/2002 |
| JP | 2002-293783 | * | 10/2002 |
| JP | 2002-293783 | A | 10/2002 |
| JP | 2006089444 | A | 4/2006 |
| WO | WO 99-19158 | | 4/1999 |

OTHER PUBLICATIONS

PCT International Search Report for PCT/JP2004/015451 mailed on Nov. 22, 2004.
Sho Yamazaki, et al., "Vulcanization Performance of Tetrasulfide Polymer", The Society of Rubber Industry, Japan, 1981 Research Presentation Conference, Abstracts, pp. 53, 2-17.

* cited by examiner

Primary Examiner—Ling-Siu Choi
(74) Attorney, Agent, or Firm—Connolly Bove Lodge & Hutz LLP

(57) ABSTRACT

A rubber composition containing 100 parts by weight a sulfur-vulcanizable rubber (A) and 0.1 to 30 parts by weight of a vulcanization agent of a cyclic polysulfide (B) having the formula (I):

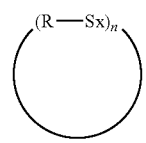

wherein R is a substituted or unsubstituted $C_2$ to $C_{20}$ alkylene group, substituted or unsubstituted $C_2$ to $C_{20}$ oxyalkylene group or alkylene group having an aromatic ring, n is an integer of 1 to 20, x is a number of 2 to 6 on average.

11 Claims, 1 Drawing Sheet

RUBBER COMPOSITION CONTAINING CYCLIC POLYSULFIDE AS VULCANIZATION AGENT AND PNEUMATIC TIRE USING THE SAME

TECHNICAL FIELD

The present invention relates to a rubber composition containing a cyclic polysulfide, as a vulcanization agent, and having improved various vulcanized properties of sulfur-vulcanizable rubber (for example, in some cases in combination with other specific components, heat aging resistance, heat buildup, breakage characteristics, fatigue resistance characteristics, wet performance, grip performance, ice and snow brakeability, high speed durability, rolling resistance, lateral stability, high hardness, high strength, high elongation, etc.) and a pneumatic tire using the same.

BACKGROUND ART

Since cross-linked rubbers obtained by vulcanization with sulfur include polysulfide bonds, the heat resistance and vulcanization reversion thereof are poor. To improve these problems of heat resistance and vulcanization reversion, it is known that vulcanization agents such as a tetrasulfide polymer or cyclic polysulfide are effective (Sho Yamazaki, et al.: The Society of Rubber Industry, Japan, 1981 *Research Presentation Conference Abstracts*, P. 532-17 and Japanese Unexamined Patent Publication (Kokai) No. 10-120788). In particular, a cyclic polysulfide is preferable in terms of cross-linking efficiency, but the production methods of cyclic polysulfides reported until now involve problems such as long production processes, use of expensive materials, etc., and therefore, lack practicality (i.e., Japanese Unexamined Patent Publication (Kokai) No. 58-122944 and Japanese Unexamined Patent Publication (Kokai) No. 2002-293783).

In recent years, pneumatic tires have been improved in various ways. Among these improvements, to raise the heat aging resistance, Japanese Unexamined Patent Publication (Kokai) No. 6-57040 proposes a method of EV cross-linking (i.e., blending in a large amount of a vulcanization accelerator to reduce the ratio of polysulfide bonds), but this had the problem that dynamic fatigue resistance is inferior. Therefore, a method of resolving this tradeoff between the heat aging resistance and the dynamic fatigue resistance is described in Japanese Unexamined Patent Publication (Kokai) No. 2002-293783, but the situation is still insufficient.

Further, as a tire tread rubber for a pneumatic tire, since the improvement of the abrasion resistance or grip is necessary, a rubber composition having a large tensile strength or elongation at break had been sought. On the other hand, tire tread rubber easily degrades. Along with aging, the tread hardens and the grip is decreased. Not only that, in some cases, there was even the danger of the tread peeling off etc. To improve the sustainability of the grip of high performance tires, for example, studies have been conducted on the use of vulcanization agents or vulcanization accelerators, but in particular in rubber compositions having large amounts of filler, it is not possible to satisfy both a grip and its sustainability at satisfactory levels (see Japanese Unexamined Patent Publication (Kokai) No. 2001-348461 and Japanese Unexamined Patent Publication (Kokai) No. 10-151906).

For undertread rubber, to improve the high speed durability, a rubber composition providing a high tensile strength and elongation at break had been sought. On the other hand, a high hardness undertread for improving the steering stability and a low tan δ undertread for improving the fuel efficiency have also been sought. These physical properties were in a tradeoff. From this viewpoint, a rubber composition providing a high hardness and high strength and elongation and not causing a rise in tan δ has been sought.

Further, among the various improvements made to pneumatic tires in recent years, for bead filler rubber, to improve the fatigue resistance, a rubber composition providing a high tensile strength and elongation at break has been sought (e.g., see Japanese Unexamined Patent Publication (Kokai) No. 2002-105249). On the other hand, a high hardness undertread for improving the steering stability and a low tan δ undertread for improving the fuel efficiency have also been sought (e.g., see Japanese Unexamined Patent Publication (Kokai) No. 5-51487). These physical properties were in a tradeoff. From this viewpoint, a rubber composition providing a high hardness and high strength and elongation and not causing the increase in tan δ has been sought.

There is a need for a pneumatic tire which has an emergency running capability enabling it to be run on for a certain distance, even when punctured, bursting, etc. during use on an automobile etc. and rapidly decreasing internal pressure, that is, a run flat tire. To satisfy this need, various proposals have been made. As such a proposal, for example, Japanese Unexamined Patent Publication (Kokai) No. 10-297226 and Japanese National Publication (Tokuhyo) No. 2001-519279 disclose the technology of fitting a run flat support (core ring) over the rims at the inside cavity of a pneumatic tire and using the same to support a punctured or otherwise damaged pneumatic tire so as to enable run flat operation. The rubber used for the side reinforcement layers of such run flat tires is required to feature low heat buildup and high hardness, and therefore large amounts of polybutadiene rubber (BR) have been blended or high cross-linking density formulations have been used. However, the side reinforcement rubber is required to feature strong heat resistance and fatigue resistance, and therefore, if trying to raise the heat resistance by EV cross-linking (that is, blending of a larger amount of vulcanization accelerator than the sulfur to increase the ratio of mono and disulfide bonds), the flex fatigue strength becomes inferior, while conversely if using ordinary cross-linking (that is, increasing the amount of sulfur over the accelerator and increasing the ratio of polysulfides), the flex fatigue strength is improved, but the heat resistance or aging properties become poor, that is to say, there was a problem of antinomy.

Further, side reinforcement rubber formulations contain large amounts of polybutadiene rubber, and therefore even new products (before aging) are low in elongation at break, and therefore there was a limit to the run flat durability after long use (after aging). Further, since run flat tires have thick side parts, at the time of vulcanization, heat conduction inside the tire is difficult. In the case of high temperature vulcanization, a large difference results in the physical properties near the surface and inside, while there was the problem of poor productivity at a low temperature vulcanization.

A run flat core ring 1, as shown in FIG. 1, is arranged in the inner cavity 3 of a pneumatic tire 2, is composed of a ring-shaped metal shell 4 and an elastic ring 5, and is supported at the rim 6. The elastic ring of a run flat core ring is required to have a low heat buildup and high hardness, but, if increased in hardness (the increase in cross-linking density), while maintaining the low heat buildup, the elongation at break become small, and, therefore, there was a problem of a limit to the durability during run flat operation. Further, the elastic ring of the core ring 1 is in constant contact with the rim, so the heat generated from the brake at the time of normal operation is transmitted to the rims which are therefore exposed to a considerably high temperature over a long time. Therefore, if the heat aging resistance of the rubber is poor, there has been the problem of the desired performance unable to be exhibited in the run flat state.

Further, the inner liners of pneumatic tires generally use butyl rubbers such as butyl rubber or halogen butyl rubber (e.g., see Japanese Unexamined Patent Publication (Kokai) No. 10-87884), but butyl rubber is poor in reinforcability with carbon black, etc., and therefore, compositions of butyl rubber are inferior in mechanical properties and are limited in applications of use.

Further, belt coat compounds of pneumatic tires are required to provide high rigidity, but if trying to increase the rigidity by increasing the amount of carbon black or increasing the amount of the sulfur serving as the vulcanization agent or vulcanization accelerator, the elongation is decreased and the fatigue resistance is decreased. As a result, separation occurs at the ends of the belt and problems occur in the tire, and therefore, securing of high rigidity and elongation is necessary (Japanese Unexamined Patent Publication (Kokai) No. 2001-226528). Further, to impart a high bonding, blending of a large amount of sulfur is proposed (Japanese Unexamined Patent Publication (Kokai) No. 2000-233603), but this induces deterioration of the heat aging resistance. To increase the heat aging resistance, an antioxidant may be increased, but this has the problem of being liable to impair bonding with wire (metal).

DISCLOSURE OF THE INVENTION

Accordingly, the object of the present invention is to solve the various problem points in the conventional pneumatic tire industry, by using a cyclic polysulfide instead of at least part of the conventional sulfur vulcanization, and to provide a rubber composition having the improved various types of physical properties of vulcanized rubber and a pneumatic tire using the same.

In accordance with the present invention, there is provided a rubber composition comprising (A) 100 parts by weight of a sulfur-vulcanizable rubber and (B), as a vulcanization agent, 0.1 to 30 parts by weight, of a cyclic polysulfide of the formula (I):

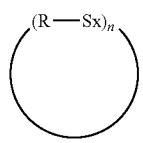

(I)

wherein R is a substituted or unsubstituted $C_2$ to $C_{20}$ alkylene group, substituted or unsubstituted $C_2$ to $C_{20}$ oxyalkylene group or alkylene group having an aromatic ring, n is an integer of 1 to 20 and x is an average number of 2 to 6.

BRIEF DESCRIPTION OF THE DRAWINGS

The present invention will now be explained, while referring to the drawing, wherein.

BEST MODE FOR CARRYING OUT THE INVENTION

Figure 1:
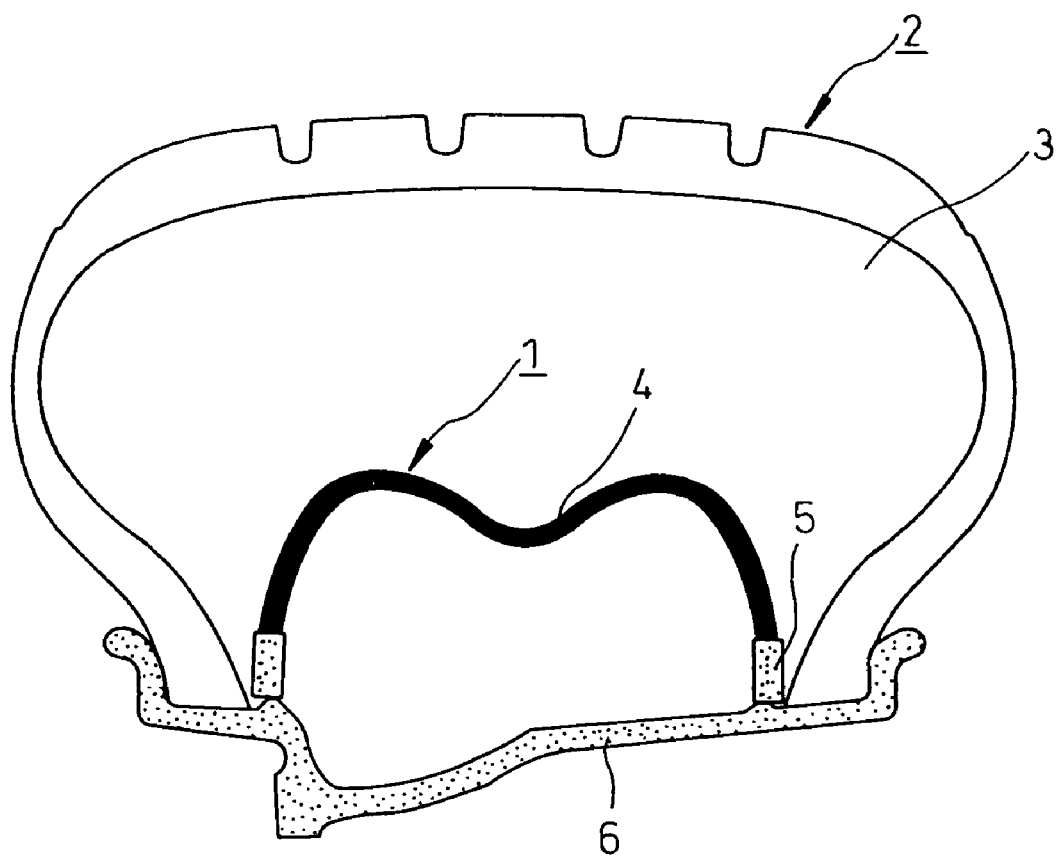
FIG. 1 is a cross-sectional view along the meridial direction showing principal parts of an embodiment of a tire wheel core ring according to the present invention.

In the description and in the attached claims, the singular forms ("a", "an", "the") used should be understood as including the plural form, except when clearly not so from the context.

In the present invention, as the vulcanization agent in the rubber composition, at least part of the conventional sulfur (in some cases all) is replaced with the (B) cyclic polysulfide having the formula (I). Such a cyclic polysulfide can be, for example, produced in the following way. That is, the cyclic polysulfide having the formula (I) is produced by reacting a dihalogen compound having the formula: X—R—X, wherein X independently represents fluorine, chlorine, bromine or iodine, preferably a chlorine or bromine halogen atom, R represents a substituted or unsubstituted $C_2$ to $C_{20}$ alkylene group, substituted or unsubstituted $C_2$ to $C_{20}$ oxyalkylene group or alkylene group including an aromatic ring, preferably the substituted or unsubstituted $C_2$ to $C_{18}$, more preferably a $C_4$ to $C_{10}$ alkylene group, as these substituent groups, phenyl, benzyl, vinyl, silyl, epoxy, isocyanate, etc. may be mentioned and an alkali metal polysulfide M-$S_x$-M, wherein, M is an alkali metal, for example, sodium, potassium, lithium, etc., and x is an integer of 2 to 6, preferably 3 to 5, in a hydrophilic solvent or a non-compatible mixed solvent of hydrophilic and lyophilic solvents, as a two-phase system reaction or by adding, in an M-$S_x$-M solution (as the solvent water or a $C_1$ to $C_4$ aliphatic alcohol can be used and the use of water is most preferable), X—R—X at a rate so that M-$S_x$-M and X—R—X react at their interfaces (see Japanese Unexamined Patent Publication (Kokai) No. 2002-293783). Note that, if the rate of addition of X—R—X in the latter method is too fast, the concentration of X—R—X becomes higher, a reaction occurs also other than at the interfaces, intermolecular reactions are given priority to form linear chains, so this is not preferred. Accordingly, reacting M-$S_x$-M and X—R—X as much as possible in a nonhomogeneous system just at the interfaces is preferable for obtaining cyclic polysulfide.

As the group R of said general formula X—R—X and the formula (I), for example, linear or branched alkylene group such as ethylene, propylene, butylene, pentylene, hexylene, octylene, nonylene, decylene, 1,2-propylene may be mentioned. These alkylene groups may also be substituted with a substituent group such as a phenyl group, benzyl group. As the group R, further, an alkylene group including an oxyalkylene group, for example, an alkylene group including an oxyalkylene group to which a group ($CH_2CH_2O$)p and group ($CH_2$)q, wherein p is an integer of 1 to 5 and q is an integer of 0 to 2, are freely bonded may be used. Preferable groups R include —$CH_2CH_2OCH_2CH_2$—, ($CH_2CH_2O)_2CH_2CH_2$—, ($CH_2CH_2O)_3CH$ —$CH_2$—, ($CH_2CH_2O)_4CH_2CH_2$—, ($CH_2CH_2O)_5CH_2CH_2$—, ($CH_2CH_2O)_2CH_2$—, —$CH_2CH_2OCH_2OCH_2CH_2$—, wherein, in particular x is preferably on average, 3 to 5 is, 3.5 to 4.5 is more preferable. n is preferably an integer of 1 to 15, more preferably 1 to 10, still more preferably an integer of 1 to 5.

The reaction between the dihalogen compound and the alkali metal polysulfide is an equivalent amount reaction. In practice, the two compounds are reacted in 0.95:1.0 to 1.0: 0.95 (equivalent amount ratio), at a temperature of, preferably 50 to 120° C., more preferably 70 to 100° C.

The hydrophilic solvent or noncompatible mixed solvent of the hydrophilic/lyophilic solvents used in the present invention is not particularly limited. In the actual reaction system, a hydrophilic solvent alone or any insoluble mixed solvent system forming two phases may be used. Specifically, for example, as a hydrophilic solvent, in addition to water, methanol, ethanol, ethylene glycol, diethylene glycol, or another alcohol may be mentioned. These may be used in any mixtures. Further, as the lyophilic solvent used mixed with these hydrophilic solvents, toluene, xylene, benzene, and other aromatic hydrocarbons, pentane, hexane, and other aliphatic hydrocarbons, dioxane, dibutyl ether or other ethers, ethyl acetate, or other esters, etc. may be mentioned. These may be used in any mixtures.

The reaction between the dihalogen compound and the alkali metal polysulfide in a hydrophilic solvent or in a noncompatible mixed solvent system at the interfaces is an equivalent amount reaction. In practice, the two compounds are reacted at 0.95:1 to 1:0.95 (equivalent amount ratio). The reaction temperature is preferably 50 to 120° C., more preferably 70 to 100° C. The dihalogen compound to be reacted is preferably composed of two or more types of dihalogen compounds. Therefore, as the dihalogen compound, for example, a mixture of dichloroethyl formal and dichloroethane is preferable, while as the metal sulfide, for example, sodium polyhydride is preferable.

In the above reaction, no catalyst is required, but in some cases, as the catalyst, a quaternary ammonium salt, phosphonium salt, crown ether, etc. may be used. For example, $(CH_3)_4N^+Cl^-$, $(CH_3)_4N^+BR^-$, $(C_4H_9)_4N^+Cl^-$, $(C_4H_9)_4N^+BR^-$, $C_{12}H_{25}N^+(CH_3)_3BR^-$, $(C_4H_9)_4P^+BR^-$, $CH_3P^+(C_6H_5)_3I^-$, $C_{16}H_{33}P^+(C_4H_9)_3BR^-$, 15-crown-5, 18-crown-6, benzo-18-crown-6, etc. may be used. In particular, when producing an alkylene skeleton cyclic polysulfide (B), a catalyst is preferably used.

The cyclic polysulfide (B) used in the present invention is blended into 100 parts by weight of diene-based rubber in an amount of 0.1 to 20 parts by weight, preferably 0.5 to 20 parts by weight. If the amount blended is too small, the effect thereof as a vulcanization agent is not manifested, the strength of the vulcanized rubber is decreased, etc., so this is not preferred, while conversely if too large, the vulcanization degree is increased too much and the viscosity is decreased too much, so this is not preferred.

As the sulfur-vulcanizable rubber used as the ingredient (A) in the present invention, any rubber generally used in the past for tires or other uses, for example, diene-based rubbers such as various types of natural rubber (NR), various types of polyisoprene rubber (IR), various types of polybutadiene rubber (BR), various types of styrene-butadiene copolymer rubber (SBR), acrylonitrile-butadiene copolymer rubber, chloroprene rubber (CR), and their partial hydrogenates or (halogenated) butyl rubber (IIR), ethylene-propylene diene copolymer rubber (EPDM), acryl rubber (ACM), etc. may be mentioned. These may be used alone or in any mixtures thereof.

In the first aspect of the present invention, for the purpose of developing a rubber composition excellent in the heat aging resistance and heat buildup of the vulcanized rubber, there is provided a rubber composition including, as said sulfur-vulcanizable rubber, natural rubber and/or polyisoprene rubber in an amount of 100 parts by weight, and, as a vulcanization agent, a cyclic polysulfide having the formula (I), wherein R is $-(CH_2)_m-$, wherein m is an integer of 2 to 20, n is an integer of 1 to 15, preferably 1 to 10, more preferably 1 to 5 and x is a number of an average of more than 4 to 6 in an amount of 1 to 30 parts by weight.

In the first aspect of the present invention, as shown also in the following examples, there is provide a rubber composition excellent in heat aging resistance and heat buildup using natural rubber and/or polyisoprene.

The cyclic polysulfide, as explained above, for example, is produced by reacting a dihalogen compound having the formula:

$$X-(CH_2)_n-X$$

wherein, X, independently, represents, fluorine, chlorine, bromine, or iodine, preferably chlorine or bromine halogen atoms and n is 2 to 20, preferably 4 to 12, and an alkali metal polysulfide $MS_x$-M, wherein M is an element belongs to Group IA of the Periodic Table, for example, sodium, potassium, lithium, or another alkali metal, and x is a number of an average larger than 4 to 6, preferably a number of, on average, about 4.5 to about 5 in a hydrophilic or in a noncompatible mixed solvent of hydrophilic and lyophilic solvents as a two phase system reaction or by reaction in a solution of M-$S_x$-M, as the solvent, water and a $C_1$ to $C_4$ aliphatic alcohol may be used, and use of water is most preferred, by adding $X-(CH_2)_n-X$ at a rate for a reaction at the interface of the solvents. Note that, in the latter method, if the rate of addition of $X-(CH_2)_n-X$ is too fast, the concentration of $X-(CH_2)_n-X$ is increased, a reaction also occurs other than at the interfaces, intermolecular reactions are given priority to form linear chains, so this is not preferred. Therefore, performing the reaction between the M-$S_x$-M and $X-(CH_2)_n-X$ as much as possible in a nonhomogeneous system just at the solvent interface is preferable for the production of a cyclic polysulfide.

In a preferable mode of the present invention, the cyclic polysulfide having the formula (I), wherein n number of R's, independently, represent a substituted or unsubstituted $C_2$ to $C_{20}$ alkylene group, substituted or unsubstituted $C_2$ to $C_{20}$ oxyalkylene group, or alkylene group including an aromatic ring, X is preferably an average of 3 to 5 and n is preferably 1 to 15, more preferably 1 to 10 is obtained by reacting at least two types of dihalogen compounds having the formula (II):

$$X-(CH_2)_n-X \qquad (II)$$

wherein X represents a halogen atom and n is an integer of 2 to 20, for example, dichloroethyl formal or dichloroethane and a metal polysulfide having a formula (III):

$$M-S_x-M \qquad (III)$$

wherein M is a metal belonging to Group IA of the Periodic Table, and X is a number of an average or more than 3 to 6, (e.g., sodium polysulfide) in a hydrophilic solvent or a noncompatible mixed solvent of a hydrophilic solvent and a lyophilic solvent insoluble in the presence or absence of a phase-transfer catalyst, at a temperature of 50 to 150° C., preferably 50 to 120° C. This cyclic polysulfide, compared with the case of using one type of a dihalogen compound, provides a low viscosity, high vulcanization efficiency vulcanization agent.

In the present invention, the above reaction is preferably carried out in the presence of a suitable phase-transfer catalyst at a temperature of 50 to 150° C., preferably 50 to 120° C. As examples of phase-transfer catalysts, a quaternary ammonium salt, phosphonium salt, crown ether, aliphatic acid metal salt, etc. may be used. For example, $(CH_3)_4N^+Cl^-$, $(CH_3)_4N^+BR^-$, $(C_4H_9)_4N^+Cl^-$, $(C_4H_9)_4N^+BR^-$, $C_{12}H_{25}N^+(CH_3)_3BR^-$, $(C_4H_9)_4P^+BR^-$, $CH_3P^+(C_6H_5)_3I^-$, $C_{16}H_{33}P^+(C_4H_9)_3BR^-$, 15-crown-5, 18-crown-6, benzo-18-crown-6, or $RCOO^-Na^+$, $RSO_3^-Na^+$, $(RO)_2PO_2^-Na^+$, wherein, R represents an alkyl group, etc. may be mentioned.

The rubber composition in the first aspect of the present invention comprises natural rubber and/or polyisoprene in an amount of 100 parts by weight, into which the cyclic polysulfide (B) having the formula (I) is blended in an amount of 0.5 to 30 parts by weight, preferably 0.5 to 10 parts by weight. The rubber vulcanization agent of the present invention can be used, together with vulcanization agents such as conventional sulfur. If the amount of the cyclic polysulfide (B) is too small, a sufficient vulcanization effect is not obtained and the vulcanized rubber drops in strength, and therefore this is not preferred, while conversely if too large, the vulcanized rubber becomes hard, and therefore this is not preferred.

The rubber composition of the first aspect of the present invention may contain, in addition to the above essential ingredients, various types of additives generally blended for tire use or other general rubber uses, for example, fillers such as carbon black or silica, a vulcanization accelerator, various types of oil, an anti-oxidant, a plasticizer. These additives may be mixed and vulcanized to obtain compositions in general manners which are used for vulcanization or cross-linking. The amounts of these additives may be made the general amounts used in the past so long as the object of the present invention is not adversely affected.

In a second aspect of the present invention, for the purpose of improving the breaking characteristics and providing a rubber composition excellent in fatigue resistance and further improved in aging resistance, there are provided a rubber composition containing, 100 parts by weight of, a sulfur-vulcanizable rubber (A) 0.5 to 5 parts by weight of a cyclic polysulfide (B) having the formula (I), wherein x is a number of, on average, 2 to 6, n is an integer of 1 to 15, preferably 1 to 10, more preferably 1 to 5, R is a substituted or unsubstituted $C_2$ to $C_{20}$ alkylene group, substituted or unsubstituted $C_2$ to $C_{20}$ oxyalkylene group or alkylene group containing an aromatic ring, and a vulcanization accelerator (C) in an amount providing a weight ratio of (C)/(B) of 1 or more as well as a pneumatic tire using the rubber composition.

The second aspect of the rubber composition according to the present invention uses the cyclic polysulfide, as a vulcanization agent, and therefore, can give high breaking characteristics both before aging and after aging, exhibit high breaking characteristics even when vulcanized at a high temperature, and further improve the viscoelastic characteristics.

The cyclic polysulfide (B) having the formula (I) used in the present invention may be produced by the above-mentioned method.

The rubber composition of the present invention contain 0.5 to 5 parts by weight, preferably 0.8 to 3 parts by weight of, the cyclic polysulfide (B), based upon 100 parts by weight of rubber. If the amount is too small, the desired effect cannot be obtained, while conversely if too large, scorching easily occurs and the cost also increases and therefore this is not preferred.

The rubber composition according to the present invention contains as the component (C) a vulcanization accelerator in an amount providing a weight ratio (C)/(B) with the component (B) of 1 or more, preferably 1 to 5. If the amount is too small, the desired effect cannot be obtained, while conversely if too large, sufficient vulcanization is not performed and the rubber properties are damaged, and therefore this is not preferred.

As the vulcanization accelerator to be blended into the rubber composition of the present invention, as the component (C), any compound used as a vulcanization accelerator in the past in the rubber industry may be used, but a sulfenamide-based, thiuram-based, benzothiazole-based, dithiocarbamate-based, guanidine-based vulcanization accelerator is preferable.

The rubber composition according to the present invention may use any sulfur generally used in the past as a vulcanization agent, together with the cyclic polysulfide (B). When using sulfur (D), together with the ingredient (B), it is preferably used in an amount providing a (D)/(B) (weight ratio) of 5 or less, preferably 2 or less. If this ratio is too large, the desired effect of the present invention is liable to be difficult to obtain, and therefore this is not preferred.

The rubber composition according to the present invention may be shaped by ordinary methods for use for a pneumatic tire cap tread, belt coat, bead filler, sidewall, undertread, carcass coat, rim cushion, and finishings or, in addition to pneumatic tires, various types of other applied products such as a rubber hose, marine hose, fender, track belt, conveyor belt.

In the third aspect of the present invention, for eliminating the problems in the prior art and providing a rubber composition having a large strength and elongation, capable of sustaining the performance over a long period, and useful as a tire tread part of a pneumatic tire, and a pneumatic tire using the same, according to a first mode, there is provided a tire tread rubber composition including a sulfur-vulcanizable rubber mainly composed of an aromatic vinyl-diene copolymer rubber in an amount of 100 parts by weight and a cyclic polysulfide having the formula (I), wherein x is a number of an average 2 to 6, n is an integer of 1 to 20, R is a substituted or unsubstituted $C_2$ to $C_{20}$ alkylene group, substituted or unsubstituted $C_2$ to $C_{20}$ oxyalkylene group or alkylene group having an aromatic ring in an amount of 0.1 to 10 parts by weight.

Further, according to the second mode, there is provided a tire tread rubber composition containing a diene-based rubber ingredient in an amount of 100 parts by weight, carbon black and/or silica in a total amount of 100 to 200 parts by weight, and a cyclic polysulfide having the formula (I), wherein x is a number of an average 2 to 6, n is an integer of 1 to 20, R is a substituted or unsubstituted $C_2$ to $C_{20}$ alkylene group, substituted or unsubstituted $C_2$ to $C_{20}$ oxyalkylene group, or alkylene group including an aromatic ring, and sulfur in a total amount of 0.5 to 5 parts by weight and in a ratio of the amount of cyclic polysulfide with respect to the total weight of the cyclic polysulfide and sulfur of 0.1 to 2 (weight ratio).

Further, according to a third mode, there is provided a tire tread rubber composition suitable for ice and snow containing a sulfur-vulcanizable rubber mainly comprised of natural rubber and/or polybutadiene rubber in an amount of 100 parts by weight, a cyclic polysulfide having the formula (I), wherein, x is a number of an average 2 to 6, n is an integer of 1 to 20, R is a substituted or unsubstituted $C_2$ to $C_{20}$ alkylene group, substituted or unsubstituted $C_2$ to $C_{20}$ oxyalkylene group, or alkylene group including an aromatic ring, in an amount of 0.1 to 10 parts by weight, and a softening agent of a weight average molecular weight converted to polystyrene of 100,000 or less in an amount of 10 to 100 parts by weight.

Still further, according to a fourth mode, there is provided a pneumatic tire with a tread having a structure of two or more layers comprised of a cap part contacting the road surface and a base part at the inside of the same, the pneumatic tire using for the base part of the tread a rubber composition comprised of sulfur-vulcanizable rubber in an amount of 100 parts by weight, silica and/or carbon black in a total amount of 30 to 100 parts by weight, and a cyclic polysulfide having the formula (I), wherein, x is a number of an average 2 to 6, n is an integer of 1 to 20, R is a substituted or unsubstituted $C_2$ to $C_{20}$ alkylene group, substituted or unsubstituted $C_2$ to $C_{20}$ oxyalkylene group or an alkylene group including an aromatic ring, in an amount of 0.1 to 10 parts by weight.

Each rubber composition in the third aspect of the present invention uses the cyclic polysulfide, as a vulcanization agent, whereby the grip performance, breaking strength, grip sustainability, durability and steering stability can be improved.

The cyclic polysulfide having the formula (I) blended into the rubber compositions of the first to fourth modes in the third aspect of the present invention may be produced by the above-mentioned method.

The rubber composition in the third aspect of the present invention contains therein the cyclic polysulfide (B) in an amount, based upon 100 parts by weight of the rubber (A), of 0.1 to 10 parts by weight, preferably 0.2 to 8 parts by weight. If the amount is too small, the desired effect cannot be obtained, while conversely if too large, scorching easily occurs and the cost also increases, and therefore this is not preferred. However, in the second mode of the present invention, it is blended in so that the total amount of the cyclic polysulfide and sulfur becomes 0.5 to 5 parts by weight, preferably 0.6 to 4.8 parts by weight and so that the ratio of the amount of cyclic polysulfide, based upon the total amount of the cyclic polysulfide and sulfur becomes 0.1 to 2 (weight ratio), preferably 0.2 to 1.9 (weight ratio).

As the aromatic vinyl-diene based copolymer rubber used in the first mode, for example, various types of styrene-butadiene copolymer rubber (SBR), styrene-isoprene copolymer rubber, styrene-isoprene-butadiene copolymer rubber, etc. may be used. Use of the rubber having a glass transition temperature (Tg) of −40° C. to 0° C. is preferable. The aromatic vinyl-diene based copolymer is preferably blended into the rubber composition in an amount of 40 to 100% by weight, more preferably 45 to 100 wt %. As other rubber ingredients, for example, natural rubber (NR), polyisoprene rubber (IR), polybutadiene rubber (BR), acrylonitrile-butadiene copolymer rubber (NBR), butyl rubber, halogenated butyl rubber, etc. may be mentioned.

The rubber composition of the first mode may further contain therein silica and/or carbon black used in rubber compositions in the past (total amount, based upon 100 parts by weight of rubber component, of 55 parts by weight to less than 100 parts by weight is preferable, 60 to 98 parts by weight is more preferable). As the carbon black, the nitrogen specific surface area ($N_2SA$, measured according to ASTM D3037) is preferably, 80 $m^2/g$ to less than 150 $m^2/g$, more preferably 82 to 148 $m^2/g$.

In the second mode, as the diene-based rubber contained, together with the cyclic polysulfide, any diene-based rubber used in tire rubber compositions in the past may be used, specifically, natural rubber (NR), various types of polyisoprene rubber (IR), various types of polybutadiene rubber (BR), various types of styrene-butadiene based copolymer rubber (SBR), styrene-isoprene copolymer rubber and acrylonitrile-butadiene copolymer rubber. These may be used alone or in any mixture thereof. Among these, SBR is preferably used in an amount of 70% by weight or more of the rubber ingredient.

In the second mode, it is possible to further contain any carbon black and/or silica usable for tires in the past, as a total amount, based upon 100 parts by weight of the diene-based rubber component, of preferably 100 to 200 parts by weight, more preferably 102 to 190 parts by weight. If the amount of the filler is small, the grip performance is not sufficient, while conversely if too large, the mixability and workability deteriorate, and therefore this is not preferred. Note that, as the carbon black, those having an $N_2SA$ of 150 to 300 $m^2/g$ is preferable from the viewpoint of the high grip performance.

In the second mode, as explained above, there is provided a tire tread rubber composition containing the cyclic polysulfide having the formula (I) in an amount providing a total amount of cyclic polysulfide and sulfur of 0.5 to 5 parts by weight, preferably 0.6 to 4.8 parts by weight, and providing a ratio of the amount of cyclic polysulfide to the total amount of the cyclic polysulfide and sulfur of 0.1 to 2 (weight ratio), preferably 0.2 to 1.9 (weight ratio). If the total amounts of the cyclic polysulfide and the sulfur is small, the grip sustainability deteriorates, while if conversely large, the grip performance is not good, and therefore this is not preferred, Further, if the amount of the cyclic polysulfide is small, the extent of improvement of the grip sustainability becomes smaller, and therefore this is not preferred.

In the second mode, further, by blending a thiuram based accelerator having a formula (IV):

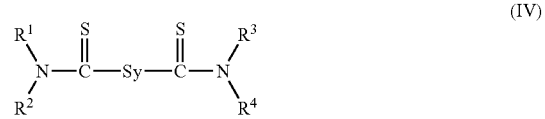

(IV)

wherein $R^1$ to $R^4$ independently indicate a $C_1$ to $C_{10}$ alkyl group or $C_1$ to $C_{20}$ alkyl group having an aromatic ring, y is an integer of 1 to 4, in an amount, based upon 100 parts by weight of the rubber component, of preferably 0.2 to 5 parts by weight, more preferably 0.3 to 4.8 parts by weight, the fatigue resistance characteristics and heat aging resistance are further improved. As preferable thiuram-based accelerators, for example, tetramethylthiuram disulfide, tetraethylthiuram disulfide, tetramethylthiuram monosulfide, tetrakis(2-ethylhexyl)thiuram disulfide, tetrabenzylthiuram disulfide, etc. may be mentioned.

In the third mode, there is provided a tire tread rubber composition suitable for ice and snow containing, together with the cyclic polysulfide, a sulfur-vulcanizable rubber mainly composed of natural rubber (NR) and/or polybutadiene rubber (BR), and a softening agent having a weight average molecular weight converted to polystyrene of 100,000 or less, preferably 5000 to 90000, in an amount of 10 to 100 parts by weight, preferably 12 to 90 parts by weight.

As the tire tread rubber, to improve the abrasion resistance or to improve the grip, a rubber composition exhibiting a high tensile strength and elongation at break has been sought. Further, the tread rubber easily deteriorates and the tread hardens along with time. In the case of snow tires, the ice and snow performance greatly decreases due to the effect of the tread. From this viewpoint, a rubber composition having a high strength and elongation and capable of sustaining the performance over a long period is necessary, but according to the present invention, for realizing sufficient grip as a snow tire tread, it is preferable that the rubber mainly compose natural rubber (NR) and that the Tg is −100° C. to −50° C. Further, the carbon black and/or the silica preferably are blended, based upon 100 parts by weight of rubber, in an amount of 40 to 100 parts by weight. In particular, the carbon black is preferably those having an $N_2SA$ of 80 $m^2/g$ to less than 150 $m^2/g$. According to the present invention, by blending a heat expandable thermoplastic resin or expandable graphite in an amount, based upon 100 parts by weight of rubber, of 1 to 15 parts by weight, the ice and snow performance is preferably improved.

The heat expandable thermoplastic resin is a heat expandable thermoplastic resin, which expands by heat to form a gas-filled thermoplastic resin and is used in an amount, based upon 100 parts by weight of the diene-based rubber, of 1 to 15 parts by weight, preferably, 2 to 10 parts by weight. If the amount is less than 1 part by weight, the desired ice and snow performance is not obtained, while conversely if more than 15 parts by weight, the abrasion resistance of the rubber composition remarkably decreases and therefore this is not preferred.

The particle size before expansion of the heat expandable thermoplastic resin is not particularly limited, but 5 to 300 μm before expansion is preferable, more preferably those with a particle size of 10 to 200 The heat expandable thermoplastic resin is composed of heat expandable thermoplastic resin particles containing, in the thermoplastic resin, a liquid vaporizing and producing a gas upon heating, that is, gas-filled thermoplastic resin particles composed of outer shells made of a thermoplastic resin, in which gas is filled, which are heated to cause the same to expand at a temperature of the expansion starting temperature or higher, normally a temperature of 130 to 190° C.

As the above heat expanding thermoplastic resin, for example, currently "Expancel 091DU-80", "Expancel 092DU-120", etc. are available from Sweden's Expancel Co. and "Matsumoto Microsphere F-85", "Matsumoto Microsphere F-100", etc. are available from Matsumoto Yushi K.K.

As the thermoplastic resin forming the outer shell ingredient of the gas-filled thermoplastic resin particles, those having an expansion starting temperature of 100° C. or more, preferably 120° C. or more, and a maximum expansion temperature of 150° C. or more, preferably 160° C. or more, is preferably used. As such a thermoplastic resin, for example, a (meth)acrylonitrile polymer and further a copolymer having a high (meth)acrylonitrile content is preferably used. As the other monomer (i.e., comonomer) in the case of such a copolymer, halogenated vinyl, halogenated pyridene, styrene-based monomer (meth)acrylate-based monomer, vinyl acetate, butadiene, vinylpyridine, chloroprene, or another monomer is used. Note that said thermoplastic resin may also be cross-linked by divinylbenzene, ethylene glycol di(meth)acrylate, triethylene glycol di(meth)acrylate, trimethylol propane tri(meth)acrylate, 1,3-butylene glycol di(meth)acrylate, allyl(meth)acrylate, triacryl formal, triallyl isocyanulate, or another cross-linking agent. Regarding the mode of cross-linking, uncross-linked is preferable, but partial cross-linking is also possible to an extent not detracting from the properties of the thermoplastic resin.

As the liquid vaporizing upon heating to produce a gas, for example, hydrocarbons such as n-pentane, isopentane, neopentane, butane, isobutane, hexane, petroleum ether, chlorinated hydrocarbons such as methyl chloride, methylene chloride, dichloroethylene, trichloroethane, trichloroethylene, or other liquids may be mentioned.

The expandable graphite usable in the present invention is contained in an amount, based upon 100 parts by weight of diene-based rubber, of 1 to 15 parts by weight, preferably 2 to 8 parts by weight and may be used, together with the heat expanding thermoplastic resin. If the amount is too small, the ice and snow performance cannot be obtained, and therefore this is not preferred, while conversely if too large, the contact area at the microlevel between the rubber surface and the ice and snow surface is decreased, and therefore the friction on the ice is decreased, and therefore this is not preferred. Further, if the amount is too large, the abrasion resistance and mechanical strength of the rubber composition, and therefore this is not preferred.

Expandable graphite is a powdery substance composed of layers of graphite particles containing therebetween a substance vaporizing upon heating and has a particle size of 30 to 600 μm, preferably 100 to 350 μm. Expanded graphite which expands upon heating at the time of vulcanization is preferable.

Expandable graphite is composed of sheets formed from carbon atoms superposed in layers and is obtained by acid treatment with sulfuric acid or nitric acid etc. (i.e., intercalation). This expandable graphite, for example, can be made to expand by vaporization of the interlayer substance upon heating to obtain expanded graphite (or foamed graphite). Since the material is hard before expansion, it is resistant to decrease the quality due to mixing. Further, since it expands irreversibly at a certain temperature, the vulcanization of the tire can easily result in the formation of foreign matter accompanied with space inside the rubber matrix. The tread of a tire using this rubber is suitably formed with surface relief at the time of abrasion. By efficiently removing the water film on the contact surface between the ice and the tire, this works to improve the frictional force on ice.

Expandable graphite is a known material and is produced by a known method of production. In general, it is produced by dipping graphite particles into a mixed solution of a strong acidic substance and an oxidizing agent and inserting the acid between the layers of the graphite particles by intercalation. For example, concentrated sulfuric acid is used, as the strongly acidic substance, while nitric acid is used, as the oxidizing agent. Due to this, expandable graphite composed of layers of particles between which sulfuric acid is inserted is obtained. Expandable graphite expands by opening up the layers by the volatilization of the interlayer compound upon heat treatment. Expandable graphite using sulfuric acid for the interlayer substance usually expands by heat treatment at 300° C. or more, but expandable graphite having a decreased expansion starting temperature to 300° C. or less by modification of the interlayer substance or use or joint use of another low boiling point acid compound (e.g., nitric acid) is produced and marketed. The working temperature of a rubber composition mainly composed of a diene-based rubber covered by the present invention is 200° C. or less. In the present invention, by using expandable graphite having an expansion starting temperature of 190° C. or less, predetermined effects are exhibited.

As expandable graphite having an expansion starting temperature of 190° C. or less, for example, "Graphguard 160-50", "Graphguard 160-80", etc. made by UCAR Graphtech of the U.S. are commercially available and can be acquired from Tomoe Corporation.

"Expandable graphite" terminologically wise indicates the not-yet-expanded product right after acid treatment, but sometimes also is used to refer to the expanded form after heat treatment. The expandable graphite blended into the rubber composition of the present invention is the not-yet-expanded form before heat treatment.

In the present invention, the expandable graphite is preferably not allowed to expand in the mixing and extrusion step of the rubber composition and is made to expand in the vulcanization step. One having an expansion starting temperature of preferably 120 to 190° C., more preferably 140 to 170° C., is used. If the expansion starting temperature is less than 120° C., the expandable graphite will expand at the time of mixing or the time of extrusion and the specific gravity of the rubber will change during the process, and therefore the workability is liable to be impaired. Further, if the expansion starting temperature is more than 190° C., the working temperature at the time of vulcanization has to be set at 190° C. or more, and therefore, the heat degradation of the diene-based rubber forming the main component of the rubber composition tends to remarkably deteriorate.

On the other hand, the expandable graphite has a skeletal structure composed of carbon atoms, and therefore, is good in affinity with the rubber matrix or carbon black. There is the advantage that, even if blended into a rubber, there will be small decrease in the abrasion resistance of the vulcanized rubber.

According to the fourth mode, there is provided a pneumatic tire having a structure of at least two layers of a cap part, where the tread contacts the road surface, and a base part inside from that, the pneumatic tire using for the base part of the tread a rubber composition containing 100 parts by weight of sulfur-vulcanizable rubber, silica and/or carbon black in a total weight of 30 to 100 parts by weight, preferably 35 to 95 parts by weight and the cyclic polysulfide having the formula (I) in 0.1 to 10 parts by weight, preferably 0.2 to 8 parts by weight. This rubber composition for the base part may also be used for a tread combined with the above-mentioned rubber composition for the cap part. Here, as the vulcanizable rubber, any rubber generally used for tires and other applications in the past, for example, various types of natural rubber (NR), various types of polyisoprene rubber (IR), various types of polybutadiene rubber (BR), various types of styrene-butadiene copolymer rubber (SBR), acrylonitrile-butadiene copolymer rubber, chloroprene rubber (CR), and other diene-based rubber and their partial hydrogenates or (halogenated) butyl rubber (IIR), ethylene-propylene diene copolymer rubber (EPDM), acryl rubber (ACM), etc. may be mentioned. These may be used alone or in any mixtures thereof.

The rubber composition according to the present invention may be processed by an ordinary method for use for treads, tread bases, etc. of pneumatic tires and other various types of applications and products etc.

The rubber composition in the third aspect of the present invention may contain, in addition to said essential ingredients, various types of additives generally used for tire or other general rubber use such as another filler, vulcanization or cross-linking accelerator, various types of oil, anti-aging agent, plasticizer. This formulation is mixed and vulcanized by a general method to obtain a composition which can then be used for vulcanization or cross-linking. The amounts of these additives can be made the general amounts blended in the past so long as the object of the present invention of satisfying the storage elasticity in said range is not adversely affected.

In the fourth aspect of the present invention, for the purpose of providing a rubber composition having a high hardness, a high strength and elongation, and no rise in tan δ for use for the bead filler of a pneumatic tire, there is provided a pneumatic tire using a rubber composition composed of vulcanizable rubber including natural rubber and aromatic vinyl-conjugated diene copolymer rubber in an amount of 65% by weight or more in an amount of 100 parts by weight, silica and/or (ii) carbon black in a total amount of 50 to 120 parts by weight, and a cyclic polysulfide of said formula (I), wherein x is a number of, on average, 2 to 6, n is an integer of 1 to 15, R is a substituted or unsubstituted $C_2$ to $C_{20}$ alkylene group, substituted or unsubstituted $C_2$ to $C_{20}$ oxyalkylene group or alkylene group including an aromatic ring, in an amount of 0.1 to 10 parts by weight so as to form high hardness reinforced rubber extending at the inside of the tire sidewalls from the bead to the tire sidewalls (bead filler). The pneumatic tire contains a sulfur-vulcanizable rubber composed mainly of natural rubber, together with silica and/or carbon black, and uses the cyclic polysulfide, as a vulcanization agent, to obtain high hardness, high strength and elongation, and low heat buildup rubber composition. By using this, as the bead filler of a pneumatic tire, it is possible to improve the durability and steering stability, without causing deterioration of the rolling resistance of the pneumatic tire.

As the vulcanizable rubber used in the present invention, those containing an aromatic vinyl-conjugated diene copolymer rubber such as (i) natural rubber and (ii) styrene-butadiene copolymer (SBR) in an amount of 65% by weight or more, more preferably 70% by weight or more, in addition, any rubber generally used in the past for a tire or other use, for example, various types of polyisoprene rubber (IR), various types of polybutadiene rubber (BR), acrylonitrile-butadiene copolymer rubber, styrene-isoprene copolymer rubber, styrene-isoprene-butadiene copolymer rubber, and other diene-based rubber or butyl rubber, halogenated butyl rubber, ethylene-propylene-diene copolymer rubber, etc. may be mentioned. These may be used alone or in any mixture thereof.

The (i) silica and/or (ii) carbon black usable in the rubber composition according to the fourth aspect in the present invention is blended, based upon 100 parts by weight of rubber, in a total amount of (i) and (ii) of 50 to 120 parts by weight, preferably 55 to 115 parts by weight. If the amount is too small, the hardness of the rubber is insufficient and a high steering stability cannot be obtained, and therefore this is not preferred, while conversely if too large, the heat buildup becomes large and the rolling resistance or durability deteriorates, and therefore, this is not preferred. The ratio of blending of the component (i) and (ii) is not particularly limited, but from the standpoints of the hardness and heat buildup, the ratio of (i)/(ii) is preferably 0 to 90/100 to 10.

As the silica usable in the present invention, any silica used in the past for tires etc., for example, natural silica, synthetic silica, more specifically, precipitated silica, dry type silica and wet type silica may be used. On the other hand, for the carbon black usable in the present invention, any carbon black which has been used in the past for tires or other applications may be used, but use of those having a nitrogen specific area of 20 $m^2$/g or more is preferable, while use having one of 20 to 150 $m^2$/g is more preferable.

The rubber composition in the fourth aspect of the present invention may contain therein, in addition to the essential ingredients, based upon 100 parts by weight of rubber, a heat curing resin in an amount of preferably 1 to 30 parts by weight, more preferably 3 to 25 parts by weight, and a curing agent of the heat curing resin in an amount of preferably 0.01 to 10 parts by weight, more preferably 0.1 to 8 parts by weight. If the amounts are too small, the desired effect (i.e., improvement in the steering stability) cannot be obtained, while conversely if too large, the durability deteriorates, and therefore, this is not preferred.

The type of said heat curing resin is not particularly limited, but a rosin oil, tall oil, cashew oil, linolic acid, oleic acid, linoleic acid, or other oil modified novolac type phenol-based resin or xylene, mesitylene or other aromatic hydrocarbon modified novolac type phenol based resin and nitrile rubber or other rubber modified novolac type phenol based resin may be mentioned.

Methylene donors usable as a curing agent of the above heat curing resins include hexamethylene tetramine and methylolated melamine derivatives. For example, hexamethylol melamine, hexakis (ethoxymethyl) melamine, hexakis(methoxymethyl) melamine, N,N',N''-trimethyl-N,N',N''-trimethylol melamine, N,N',N''-trimethylol melamine, N-methylol melamine, N,N'-bis(methoxymethyl) melamine, N,N',N"-tributyl-N,N',N"-trimethylol melamine, etc. may be illustrated.

The cyclic polysulfide having the formula (I) blended into the rubber composition in the present invention may, for example, be produced by the above-mentioned method.

The rubber composition in the fourth aspect of the present invention contain therein 0.1 to 10 parts by weight, preferably 0.2 to 8 parts by weight, of the cyclic polysulfide (C), based upon 100 parts by weight of rubber. If the amount is too small, the desired effect cannot be obtained, while conversely if too large, the durability becomes poor, and therefore these are not preferred.

The rubber composition according to the present invention may use, as a vulcanization agent, any sulfur generally used as a vulcanization agent in the past, together with the cyclic polysulfide (B). When using sulfur (D) together with the component (B), it is preferably used in an amount giving a (D)/(B) (weight ratio) of 8 or less, preferably 6 or less. If this ratio is too large, the desired effect of the present invention is liable to become difficult to obtain, and therefore, this is not preferred.

The rubber composition according to the present invention may contain therein, in addition to the above essential components, carbon black, a filler such as silica, various types of oil, an antioxidant, a plasticizer, various types of vulcanization accelerators, a silane coupling agent, or other various types of additives generally used for tire or other general rubber use. The blend is mixed by a general method to obtain a composition which can then be used for vulcanization. The amounts of these additives may also be made the general amounts used in the past unless the object of the present invention is not adversely affected.

In the fifth aspect of the present invention, the present invention can greatly improve on the defect of the side reinforcement rubber of a run flat tire, that is, the low elongation at break, and achieve both heat resistance and fatigue resistance. Further, for the purpose of improving the aging resistance as well, there is provided a run flat tire side reinforcement rubber composition containing (i) 100 parts by weight of a rubber containing at least 50 parts by weight of a polybutadiene rubber having a glass transition temperature (Tg) of −80° C. or less, (ii) 20 to 70 parts by weight of carbon black with a nitrogen specific area ($N_2SA$) of 70 $m^2/g$ or less, and (iii) 2 to 15 parts by weight of a cyclic polysulfide having the formula (I), wherein x is a number, on average, 2 to 6, n is an integer of 1 to 15, R is a substituted or unsubstituted $C_2$ to $C_{20}$ alkylene group, substituted or unsubstituted $C_2$ to $C_{20}$ oxyalkylene group or alkylene group including an aromatic ring, obtained by reacting a dihalogen compound having a formula: X—R—X, wherein X independently indicate a halogen atom, R a substituted or unsubstituted $C_2$ to $C_{20}$ alkylene group, substituted or unsubstituted $C_2$ to $C_{20}$ oxyalkylene group, or alkylene group including an aromatic ring and an alkali metal polysulfide having a formula: $M-S_x-M$, wherein M is an alkali metal and x is an integer of 2 to 6. Further, there is provided a pneumatic tire having a run flat performance using the rubber composition for the side reinforcement rubber and/or the bead filler inserted in a crescent cross-sectional shape at the inside of the side parts.

According to the fifth aspect of the present invention, by using the cyclic polysulfide as a vulcanization agent, the previous defect of the side reinforcement rubber, that is, the low elongation at break, can be remarkably reduced, while by imparting flexibility of cross-linking while reducing the ratio of the polysulfide bonds, the heat resistance and fatigue resistance can both be obtained and the aging resistance can be improved.

The rubber component usable in the fifth aspect of the present invention has to contain, based upon, a total amount of rubber of 100 parts by weight, a polybutadiene rubber (BR) having a Tg of −80° C. or less, preferably −85 to −110° C., in an amount of 50 parts by weight or more, preferably 55 to 80 parts by weight. If the amount of the BR is too small, low heat buildup cannot be satisfied, and therefore, this is not preferred.

As the rubber component usable, in addition to the polybutadiene rubber (BR), in the present invention, any diene-based rubber generally used for tires or other applications in the past, for example, natural rubber (NR), polyisoprene rubber (IR), various types of styrene-butadiene copolymer rubber (SBR), acrylonitrile-butadiene copolymer rubber (NBR) and their partial hydrogenates and modified forms, ethylene-propylene rubber (EPDM), etc. may be mentioned. These may be used alone or in any mixture thereof.

The carbon black usable in the fifth aspect of the rubber composition of the present invention may include any carbon black generally used for tires etc. in the past, but the nitrogen specific surface area thereof ($N_2SA$) (measured according to JIS K6217-2) has to be 70 $m^2/g$ or less, preferably 20 to 65 $m^2/g$. If the nitrogen specific surface area is too large, the heat buildup of the rubber becomes large and the run flat durability is degraded, and therefore, this is not preferred. The carbon black is blended, based upon 100 parts by weight of the rubber component, in an amount of 20 to 70 parts by weight, preferably 30 to 60 parts by weight. If the amount is too small, the rubber becomes too soft and cannot support the vehicle weight at the time of a puncture, and therefore, this is not preferred, while conversely if too large, the heat buildup becomes greater, and therefore, this is not preferred.

The cyclic polysulfide having the formula (I) blended into the rubber composition of the present invention may, for example, be produced in the following way.

The rubber composition according to fifth aspect of the present invention may use, if necessary, a sulfenamide-based vulcanization accelerator (e.g., N-cyclohexyl-2-benzothiazolyl sulfenamide, N-tert-butyl-2-benzothiazolyl sulfenamide, N-oxydiethylene-2-benzothiazolyl sulfenamide, N,N'-dicyclohexyl-2-benzothiazolyl sulfenamide) or a thiuram-based vulcanization accelerator (e.g., tetramethylthiuram disulfide, tetraethylthiuram disulfide, tetrabutyl thiuram disulfide, tetrabenzylthiuram disulfide, tetrakis(2-ethylhexyl) thiuram disulfide, tetramethylthiuram monosulfide, or dipentamethylene thiuram tetrasulfide) as a vulcanization accelerator in an amount, based upon 100 parts by weight of rubber, of preferably 1 to 5 parts by weight, more preferably 1.5 to 4 parts by weight, so as to increase the cross-linking efficiency and to improve both heat resistance and fatigue resistance.

The rubber composition according to the present invention may be used for the side reinforcement rubber and/or bead filler inserted in a crescent cross-sectional shape at the inside of the side parts of a run flat tire according to an ordinary method. Further, cyclic polysulfide cross-linking is resistant to reversion, so at the time of tire vulcanization, even if vulcanizing at least the inside of the sides (i.e., bladder side) at a high temperature, it is possible to reduce the change in the physical properties inside and to improve the vulcanization productivity.

The rubber composition according to the present invention may contain therein, in addition to the above essential ingredients, carbon black, silica, or another filler, a vulcanization accelerator, various types of oil, anti-aging agent, plasticizer, silane coupling agent, or other various types of additives generally used for tires or other rubber uses. The formulation may be mixed by an ordinary method to obtain a composition which may be used for vulcanization. The amounts of these additives may be made the conventional general amounts blended insofar as the object of the present invention is not adversely affected.

In the sixth aspect of the present invention, for the purpose of improving the run flat performance of the elastic ring forming the core ring of the run flat tire (e.g., durability, fatigue resistance, and heat aging resistance), there is provided a core ring of a run flat tire comprising, in a tire/rim cavity, a thin film, rigid metal shell and elastic ring supporting the rim, the core ring of the run flat tire forming the elastic ring using a rubber composition comprising sulfur-vulcanizable rubber (A) in an amount of 100 parts by weight of rubber and a cyclic polysulfide (B) having the formula (I): wherein x is a number, on average, 2 to 6, n is an integer of 1 to 15, R is a substituted or unsubstituted $C_2$ to $C_{20}$ alkylene group, substituted or unsubstituted $C_2$ to $C_{20}$ oxyalkylene group or alkylene group including an aromatic ring) and (D) sulfur in amounts giving a (D)/(B) (weight ratio) of 0 to 2.

According to a sixth aspect of the present invention, since the elongation at break of the elastic ring can be improved, while providing the high hardness for supporting the vehicle weight at the time of a puncture, it is possible to greatly improve the durability at the time of run flat operation, in particular cornering where the elastic ring is subjected to a load. Further, in a preferred embodiment combining an organic acid cobalt salt and a resol type alkyl phenol resin for bonding with the shell, even under severe operation conditions, no peeling will occur and the durability can be further improved.

The elastic ring forming the run flat tire core ring is required to have a high hardness, but the elongation is low and the ring ends up breaking during run flat operation. Incidentally, in the present invention, by using rubber including a cyclic polysulfide for the elastic ring, improvement of the run flat durability or reduction of weight is achieved and reversion does not occur even with high temperature vulcanization, and therefore, the productivity is improved. By blending the bonding ingredients, direct bonding becomes possible.

As the rubber component of the rubber composition forming the run flat core ring according to the sixth aspect of the present invention, for example, various types of natural rubber (NR), polyisoprene rubber (IR), various types of polybutadiene rubber (BR), various types of styrene-butadiene copolymer rubber (SBR), ethylene-propylene-diene three-way copolymer rubber (EPDM), nitrile butadiene rubber (NBR) and their partial hydrogenates and modified forms, etc. may be mentioned. These may be used alone or in any mixture thereof.

According to a sixth aspect of the present invention, the cyclic polysulfide (B) having the formula (I) and any ordinary sulfur (D) is blended, as vulcanization agents, preferably in a total amount of 1 to 20 parts by weight, more preferably 2.5 to 10 parts by weight, based upon 100 parts by weight of the rubber ingredient. If the amount is too small, the desired physical properties become difficult to obtain and the bonding with the metal shell is decreased, and therefore, this is not preferred, conversely while if too large, the physical properties after aging (i.e., aging resistance) is decreased, and therefore, this is not preferred. According to the present invention, further the vulcanization agents (B) and (D) have to be used in a weight ratio of (D)/(B)=0 to 2, preferably 0 to 1. If this ratio is too high, the effect of improvement of the heat aging resistance cannot be obtained, and therefore, this is not preferred.

According to a sixth aspect of the present invention, the rubber composition preferably may contain a vulcanization accelerator in an amount of 0.1 to 5 times the weight of said cyclic polysulfide (B) and any sulfur (D) in total, more preferably 0.5 to 4 times the weight, in particular a sulfenamide-based and/or thiuram-based vulcanization accelerator. If blending this vulcanization accelerator, the heat aging resistance and breaking characteristics are further improved, and therefore, this is preferable.

The cyclic polysulfide having the formula (I) blended into the rubber composition of the present invention, for example, may be produced as explained above.

As a preferable mode of the rubber composition according to the sixth aspect of the present invention, to further improve the bonding of the rubber composition with metal, it is possible to blend an organic acid cobalt salt in an amount of 0.1 to 5 parts by weight, more preferably 0.5 to 4 parts by weight and/or a resol type alkyl phenol resin in an amount of 1 to 6 parts by weight, more preferably 2 to 5 parts by weight, based upon 100 parts by weight of rubber. As the organic acid cobalt salt, for example, cobalt naphthenate, cobalt stearate, cobalt borate neodecanate, cobalt rosinate, cobalt acetyl acetonate, etc. may be mentioned. If the amount of the organic acid cobalt salt is too small, the desired effect of improvement is not recognized, while conversely if too large, the rubber properties deteriorate, and therefore, this is not preferred.

On the other hand, if the amount of the resol type alkyl phenol or resol type alkyl phenol resin is too small, the desired effect of improvement cannot be recognized, while if too large, scorching of the rubber occurs at the time of kneading or working and it is liable to be unable to be shaped, and therefore, this is not preferred.

The sixth aspect of the present invention will now be specifically explained with reference to the embodiment shown in FIG. 1. FIG. 1 is a cross-sectional view along the meridial direction showing principal parts of a typical embodiment of the tire wheel core ring of the present invention.

As shown in FIG. 1, the run flat tire core ring 1 according to the present invention is formed from a ring-shaped metal shell 4 inserted into a cavity 3 of a pneumatic tire 2 and a rubbery elastic ring 5. This run flat tire core ring 1 is shaped with an outside diameter smaller than the inside diameter of the cavity 3 so as to maintain a certain distance from the inside surface of the cavity 3 of the pneumatic tire 2. The inside diameter is formed to substantially the same dimensions as the inside diameter of the bead of the pneumatic tire. This run flat tire core ring 1 is inserted into the inside of the pneumatic tire 2 and in that state assembled together with the pneumatic tire 2 at the rims 6 of the wheel, whereby a tire wheel core ring is formed. If the tire wheel core ring is attached to an automobile, etc. and the pneumatic tire becomes punctured during operation, the punctured, flat tire 2 is supported by the outer circumference of the run flat tire core ring 1, whereby run flat operation becomes possible in that state.

As explained above, the run flat tire core ring of the tire wheel assembly according to the present invention is composed of a ring-shaped metal shell and elastic rings. The ring-shaped metal shell 4 forms a continuous support surface for supporting a punctured tire at its outside and forms left and right side walls as leg parts at its inside. The outside support surface can be shaped in various ways. For example, the shape of the horizontal cross-section perpendicular to the circumferential direction as shown in FIG. 1 may be a shape having an outwardly curved surface and also may be flat or have three or more curved surfaces aligned in the axial direction of the tire or two or more curved surfaces. It is possible to arrange in the recesses elastic rings having circular cross-sections so as to impart an impact easing action during run flat operation and/or separate the ring-shaped metal shell from the rubbery elastic, have the side walls of the metal shell directly contact the rims, and maintain the state of stable engagement. (See Japanese Patent Application No. 2002-271795). In this way, even if forming a support surface in this way, if enhancing the bonding between metal and a rubbery elastic according to the present invention, it is possible to increase the run flat operation distance of the tire.

The elastic rings are attached to the ends of the two leg parts of the ring-shaped metal shell. By abutting against the left and right rims as they are, the ring-shaped metal shell is supported. The rubbery elastic rings are composed of rubber, ease the shock or vibration received from the punctured or other tire by the ring-shaped metal shell, stop the slipping with regard to the rims and stably support the ring-shaped metal shell on the rims.

The ring-shaped metal shell 4 and the rubbery elastic rings 5 forming the run flat core ring 1 have a powerful bonding force, but preferably a predetermined bonded area should be secured. The load at the time of rim work or the time of run flat operation is made dimensionless by the rim diameter R (inch). When the bonded area is S (cm$^2$), the ratio S/R should be 4.5 cm$^2$/inch or more, preferably 8 to 20 cm$^2$/inch. Here, the "bonded area" means the bonded area between the metal and the rubbery elastic at one end of the ring-shaped metal shell, that is, the total bonded area of the front/back surfaces and the end face of the metal shell in contact with the rubbery elastic at the ends of the ring-shaped metal shape, once in the peripheral direction, at the horizontal cross-section perpendicular to the circumferential direction.

Further, the bonded surfaces between the ring-shaped metal shell 4 and the rubbery elastic rings 5 may be formed by the axial direction and the diametrical direction. The two being substantially equal is more preferable. By this, a structure capable of withstanding both force occurring in the axial direction and the diametrical direction at the time of run flat operation is formed.

In FIG. 1, the run flat core ring 1, pneumatic tire 2, and rims 6 are formed in ring shapes coaxially about the shaft of the wheel (not shown). Note that the dimensions of the metal shell 4 are not particularly limited, preferably the thickness is 0.5 to 3.0 mm and the width is the distance between the bead toes of the left and the right tires.

The tire wheel core ring of the present invention supports the weight of an automobile etc. through a flat tire, so the ring-shaped metal shell 4 is made of a metal material. As such a metal, iron, stainless steel, aluminum, titanium, their alloys, etc. may be illustrated.

When facilitating rim assembly by forming recesses or notches in the cross-sectional shape of the elastic rings, local stress concentration easily occurs. If the elongation characteristic is secured, at the time of rim assembly, there is no longer damage to the elastic rings, so this is preferably utilized. However, according to the present invention, since a cyclic polysulfide is blended, even with elastic rings having recesses or notches, since the elongation is secured, damage during the rim assembly can be prevented, and therefore, this is preferred.

According to the sixth aspect of the present invention, the rubber composition may include, in addition to the above essential components, fillers such as carbon black, silica, a vulcanization accelerator, various types of oil, an antioxidant, a plasticizer, a silane coupling agent, or other various types of additives generally blended for tire or other general rubber use. The formulation may be mixed by a general method to obtain a composition which is used for vulcanization. The amounts of blending of these additives may be made the conventional general amounts so long as the object of the present invention is not adversely affected.

In the seventh aspect of the present invention, for the purpose of improving the mechanical properties of the composition of the butyl rubber, in particular the breaking characteristics, and further improving the aging resistance as well, there is provided a rubber composition containing rubber (A) including butyl rubber or halogenated butyl rubber in an amount of 70 parts by weight or more in a total of 100 parts by weight and (ii) a cyclic polysulfide (B) having the formula (I), wherein x is a number of an average 2 to 6, n is an integer of 1 to 15, R is an alkylene group including a substituted or unsubstituted $C_2$ to $C_{18}$ alkylene group or substituted or unsubstituted $C_2$ to $C_{18}$ oxyalkylene group, obtained by reacting a dihalogen compound of the formula: X—R—X, wherein X independently indicate a halogen atom, R indicates an alkylene group including a substituted or unsubstituted $C_2$ to $C_{18}$ alkylene group or substituted or unsubstituted $C_2$ to $C_{18}$ oxyalkylene group, and a polysulfide of an alkali metal having the formula: M-$S_x$-M, wherein M is an alkali metal, x is an integer of 2 to 6, in a noncompatible mixed solvent of hydrophilic and lyophilic solvents in a two-phase system, in an amount of 0.1 to 10 parts by weight.

According to the seventh aspect of the present invention, by using the cyclic polysulfide (B) as a vulcanization agent, it is possible to remarkably improve the breaking characteristics of butyl rubber and further to improve the aging resistance.

As the rubber ingredient of the rubber composition according to the seventh aspect of the present invention, butyl rubber or halogenated butyl rubber is used in an amount, in 100 parts by weight of the rubber component, of 70 parts by weight or more, preferably 75 to 100 parts by weight. The butyl rubber or halogenated butyl rubber referred to in the present invention means an isobutylene and isoprene copolymer and its halides, an isobutylene and p-methylstyrene copolymer and its halides, etc.

Further, the butyl rubber or halogenated butyl rubber has an brittleness temperature higher than a general diene-based rubber or, depending on the formulation, around −35° C. Therefore, when used for a tire inner liner etc., in a region featuring extremely low temperatures, sometimes the inner liner reached the brittleness temperature and the rubber ended up cracking. In the past, to lower the brittleness temperature, there was the method of blending natural rubber or another diene-based rubber, but this led to a sacrifice of the low air permeability performance inherent to butyl rubber.

According to the seventh aspect of the present invention, the inventors found that, by using said cyclic polysulfide, as a vulcanization agent, the brittleness temperature of the butyl rubber is decreased. This is believed to be due to the entry of the long alkylene groups or oxyalkylene groups of the cyclic polysulfide into the cross-linking chain, whereby the increase in entropy of the cross-linking part and the greater flexibility are provided.

In the seventh aspect of the present invention, as the rubber, other than the butyl rubber or halogenated butyl rubber, for example, various types of natural rubber (NR), polyisoprene rubber (IR), various types of polybutadiene rubber (BR), various types of styrene-butadiene copolymer rubber (SBR), ethylene-propylene-diene three-way copolymer rubber (EPDM), etc. may be mentioned. These may be used alone or in any mixture thereof. If the amount of the butyl rubber or halogenated butyl rubber in the rubber component used in the present invention is less than 70 parts by weight, the inherent characteristics of the butyl rubber or halogenated butyl of the low air permeability, high hysterisis loss, etc. are impaired, and therefore, this is not preferred.

According to the seventh aspect of the present invention, the cyclic polysulfide having the formula (I) is blended as a vulcanization agent in an amount of 0.1 to 10 parts by weight, preferably 0.1 to 5 parts by weight, based upon 100 parts by weight of the rubber ingredient. If the amount is too small, the effect of improvement in the breaking characteristics or the effect of improvement in the aging resistance is not obtained, and therefore, this is not preferred, while conversely if too large, it becomes excessive with respect to the diene rubber of the butyl rubber, and therefore, the effect becomes saturated and, not only that, stickiness is caused when unvulcanized, and therefore, this is not preferred. Butyl rubbers cross-link by zinc white (zinc oxide), but it is known that, by using sulfur together with this, the physical properties become better. By using the cyclic polysulfide (I), instead of part or all of this sulfur, it is possible to remarkably improve the rubber properties. The rubber composition according to the present invention preferably uses a vulcanization accelerator in an amount 0.5 to 5 times, based upon the weight of the cyclic polysulfide, preferably a thiazole-based or sulfenamide-based, thiuram-based or other vulcanization accelerator.

The cyclic polysulfide having the formula (I) blended into the rubber composition in the seventh aspect of the present invention, for example, can be produced as explained above.

The rubber composition according to the present invention may include, in addition to the essential components, a filler such as carbon black, silica, a vulcanization accelerator, various types of oil, an antioxidant, a plasticizer, a silane coupling agent, or other various types of additives generally blended in for tire or other general rubber use. This formulation is mixed by a general method to obtain a composition which can then be used for vulcanization. The amounts of these additives may be made the conventional general amounts so long as the object of the present invention is not impaired.

In the eighth aspect of the present invention, for the purpose of improving the breaking characteristics and aging resistance of the rubber composition, a rubber composition comprising diene-based rubber in an amount of 100 parts by weight, a cobalt salt of an aliphatic or alicyclic carboxylic acid (as cobalt element) in an amount of 0.05 to 1 parts by weight and a cyclic polysulfide (C) in an amount of 0.1 to 20 parts by weight is provided.

In the eighth aspect of the present invention, as said cyclic polysulfide (C), a cyclic polysulfide having the formula (I), wherein x is a number, on average, 2 to 6, n is an integer of 1 to 20 and R is a substituted or unsubstituted $C_2$ to $C_{20}$ alkylene group, substituted or unsubstituted $C_2$ to $C_{20}$ oxyalkylene group or alkylene group having an aromatic ring, is used. This cyclic polysulfide, for example, can be produced as explained above.

In the eighth aspect of the present invention, as the vulcanization agent, the cyclic polysulfide of formula (I) is used. By replacing part or all of the sulfur, it is possible to increase the modulus and suppress changes in the physical properties after aging.

The diene-based rubber usable in the eighth aspect of the present invention may be any diene-based rubber generally used in the past for tires and other uses, for example, natural rubber (NR), polyisoprene rubber (IR), various types of polybutadiene rubber (BR), various types of styrene-butadiene copolymer rubber (SBR), acrylonitrile-butadiene copolymer rubber, hydrogenated NBR, etc. may be mentioned. These may be used alone or in any mixture thereof.

The cobalt salt of the aliphatic or alicyclic carboxylic acid blended into the rubber composition of the present invention functions as an activant for accelerating vulcanization of the rubber. As an organic acid forming that cobalt salt, for example, neodecanoic acid, stearic acid, naphthenic acid, rosin acid, tall oil acid, palmitic acid, oleic acid, linolic acid, and linoleic acid may be mentioned. Further, the organic acid may also be a boron-containing acid. For example, trineodecane borate etc. may be mentioned.

The amount of the cobalt salt of the aliphatic or alicyclic type carboxylic acid is 0.05 to 1 part by weight (converted to cobalt element), preferably 0.1 to 0.3 part by weight, based upon 100 parts by weight of diene-based rubber component. If the amount is too small, achieving the desired object is difficult, while conversely if too large, the workability deteriorates and the vulcanized rubber declines in physical properties, and therefore, this is not preferred.

The cyclic polysulfide (I) usable in the eighth aspect of the present invention is blended, based upon 100 parts by weight of the diene-based rubber, in an amount of 0.1 to 20 parts by weight, preferably 0.5 to 20 parts by weight. If the amount is too small, the effect of the vulcanization agent does not appear, the strength of the vulcanized rubber is decreased, etc., and therefore, this is not preferred, while conversely if too large, the vulcanization degree is increased too much and the viscosity is decreased too much, and therefore, this is not preferred.

The rubber composition according to the eighth aspect of the present invention, if necessary, may use sulfur or another vulcanization agent generally used in the past. When using sulfur, it is possible to replace part or a maximum of 60% of the cyclic polysulfide for use.

The rubber composition according to the eighth aspect of the present invention may contain therein, in addition to the essential ingredients, a filler such as carbon black, silica, various types of oil, an antioxidant, a plasticizer, vulcanization accelerator, silane coupling agent, or other various types of additives generally used for tire or other general rubber use. The formulation may be mixed by a general method to obtain a composition which may be used for vulcanization. The amounts of these additives may be made the conventionally generally amounts blended so long as the object of the present invention is not adversely affected.

EXAMPLES

Examples will now be used to explain the present invention further, but the scope of the present invention is by no means limited to these Examples.

Preparation Example I-1

A 30% aqueous sodium polysulfide ($Na_2S_4$) solution in an amount of 89.76 g (0.15 mol) was charged with 80 g of water, 2.4 g (0.075 mol) of sulfur and, as a catalyst, 1.16 g (0.0045 mol) of tetrabutyl ammonium bromide and reacted at 80° C. for 2 hours, then charged with 100 g of toluene and dropped with 23.3 g (0.15 mol) of 1,6-dichlorohexane at 90° C. over 1 hour and further reacted for 4 hours. After the reaction is ended, the organic phase was separated and concentrated under a reduced pressure at 90° C. to obtain a cyclic polysulfide having the formula (II) in an amount of 32.2 g (yield 94%).

$^1$HNMR (270 MHz, $CDCl_3$)δ (ppm):1.4-1.9 (8H,—$CH_2$—), 2.9-3.3 (4H,—S—$CH_2$—).

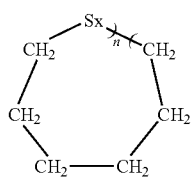

(V)

where x is an average of 4.5 and n is a number of 1 to 4.

Preparation Example I-2

A 30% aqueous sodium polysulfide ($N_{a2}S_4$) solution in an amount of 89.76 g (0.15 mol) was charged with 80 g of water, 4.8 g (0.15 mol) of sulfur and, as a catalyst, 1.16 g (0.0045 mol) of tetrabutyl ammonium bromide, reacted at 80° C. for 2 hours, then charged with 100 g of toluene 90° C. and dropped with 23.3 g (0.15 mol) of 1,6-dichlorohexane over 1 hour and further reacted for 4 hours. After the reaction is ended, the organic phase was separated and concentrated under a reduced pressure at 90° C. to obtain a cyclic polysulfide having the formula with an x of 5 on average in an amount of 35.2 g (yield 95%).

$^1$HNMR (270 MHz, $CDCl_3$)δ (ppm): 1.4-1.9 (8H,—$CH_2$—), 2.9-3.3 (4H, —S—$CH_2$—).

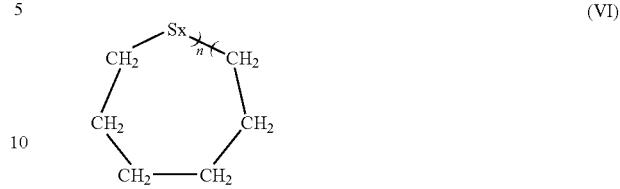

(VI)

wherein x is an average of 5 and n is a number of 1 to 4.

Examples I-1 to I-4 and Comparative Examples I-1 to I-4

Preparation of Sample

In the formulation shown in Table I-1 (parts by weight), the ingredients other than the vulcanization system were mixed in a 1.5 liter laboratory type Banbury mixer at 60 rpm for 7.5 minutes, then were mixed by an 8-inch open roll for vulcanization and vulcanized at 160° C.×20 minutes. The results are shown in Table I-1.

TABLE I-1

|  | Comp. Ex. | | | | Ex. | | | |
| --- | --- | --- | --- | --- | --- | --- | --- | --- |
|  | I-1 | I-2 | I-3 | I-4 | I-1 | I-2 | I-3 | I-4 |
| Formulation (parts by weight) | | | | | | | | |
| IR*[1] | 100 | 100 | 100 | 100 | 100 | 100 | 100 | 100 |
| Carbon black*[2] | 50 | 50 | 50 | 50 | 50 | 50 | 50 | 50 |
| Sulfur*[3] | 1 | 1 | — | — | — | — | — | — |
| CZ*[4] | 1 | 1.5 | 1 | 2 | 1 | 2 | 1 | 1.5 |
| Cyclic polysulfide*[5] | — | — | 2.6 | 2.6 | — | — | — | — |
| Cyclic polysulfide*[6] | — | — | — | — | 2.6 | 2.6 | — | — |
| Cyclic polysulfide*[7] | — | — | — | — | — | — | 2.6 | 2.6 |
| Vulcanized rubber physical properties Before aging | | | | | | | | |
| M100 (MPa)*[8] | 1.9 | 2.2 | 2.3 | 2.9 | 2.3 | 2.9 | 2.4 | 2.6 |
| M300 (MPa)*[8] | 9.8 | 11.4 | 10.8 | 13.3 | 10.8 | 13.4 | 12.0 | 13.1 |
| TB (MPa)*[9] | 25.1 | 27.6 | 29.1 | 25.6 | 28.4 | 28.9 | 29.7 | 29.8 |
| EB (%)*[9] | 569 | 562 | 626 | 494 | 605 | 552 | 607 | 563 |
| tan δ (0° C.)*[10] | 0.308 | 0.313 | 0.305 | 0.290 | 0.300 | 0.284 | 0.290 | 0.288 |
| tan δ (60° C.)*[10] | 0.223 | 0.214 | 0.233 | 0.223 | 0.219 | 0.212 | 0.207 | 0.201 |
| After aging (100° C., 72 hours) | | | | | | | | |
| M100 (MPa)*[8] | 2.8 | 3.3 | 3.0 | 3.8 | 3.2 | 3.8 | 3.4 | 3.9 |
| M300 (MPa)*[8] | 12.3 | 14.8 | 13.7 | 15.7 | 13.4 | 16.1 | 14.3 | 16.3 |
| TB (MPa)*[9] | 19.7 | 21.1 | 24.7 | 25.2 | 24.0 | 25.5 | 25.9 | 25.5 |
| EB (%)*[9] | 441 | 405 | 484 | 441 | 498 | 448 | 505 | 434 |

Notes for Table I-1
*[1]Nippon Zeon Nipol IR-2200
*[2]Tokai Carbon Seast N
*[3]Karuizawa Refinery oil extended sulfur
*[4]Ouchi Shinko Chemical Industrial Noccelar NS-F
*[5]Cyclic polysulfide synthesized in Example 3 of Japanese Unexamined Patent Publication (Kokai) No. 2002-293783 (average x = 4)
*[6]Cyclic polysulfide synthesized in Preparation Example I-1 (average x = 4.5)
*[7]Cyclic polysulfide synthesized in Preparation Example I-2 (average x = 5)
*[8]Measured based on JIS K6251 (Dumbbell No. 3)
*[9]Measured based on JIS K6251 (Dumbbell No. 3)
*[10]Measured by a Toyo Seiki Seisakusho Rheograph Solid at an initial elongation of 10%, dynamic strain of 2%, and frequency of 20 Hz (sample width 5 mm).

As is clear from the results of Table I-1, the rubber compositions of Examples I-1 to I-4 using the cyclic polysulfide of the present invention, compared with the rubber compositions of Comparative Examples I-3 and I-4, maintained their breaking strength and elongation at break, after heating aging and became lower in 60° C. tan δ as well.

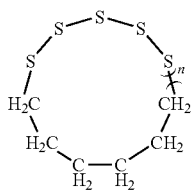

(VII)

wherein n is a number of 1 to 4.

Examples II-1 to II-3 and Comparative Example II-1

The rubber composition having each of the formulations shown in Table II-I (parts by weight) was mixed by an 8-inch open roll and the rubber vulcanized at 190° C. and 10 minutes. The results are shown in Table I. The test methods were as follows.

100% and 300% modulus: Measured according to JIS K 6251 (Dumbbell No. 3).

Breaking strength TB: Measured according to JIS K 6251.

Elongation at break EB: Measured according to JIS K 6251.

tan δ (60° C.): Measured by a Toyo Seiki Seisakusho Rheograph Solid at an initial elongation of 10%, dynamic strain of 2% and frequency of 20 Hz (sample width 5 mm).

TABLE II-1

|  | Comp. Ex. II-1 | Ex. II-1 | Ex. II-2 | Ex. II-3 |
| --- | --- | --- | --- | --- |
| Formulation (parts by weight) | | | | |
| Natural rubber*1 | 100 | 100 | 100 | 100 |
| Carbon black*2 | 50 | 50 | 50 | 50 |
| Zinc oxide*3 | 3 | 3 | 3 | 3 |
| Stearic acid*4 | 2 | 2 | 2 | 2 |
| Antioxidant*5 | 1 | 1 | 1 | 1 |
| Vulcanization accelerator*6 | 1 | 3 | 3 | 5 |
| Sulfur*7 | 1 | — | 0.5 | — |
| Cyclic polysulfide*8 | — | 1 | 0.5 | 0.5 |
| Evaluation of physical properties | | | | |
| Initial (before aging) | | | | |
| 100% modulus (MPa) | 1.7 | 2.0 | 2.0 | 2.0 |
| 300% modulus (MPa) | 9.0 | 12.7 | 12.0 | 11.6 |
| TB (MPa) | 16.1 | 24.0 | 21.2 | 19.5 |
| EB (%) | 422 | 433 | 410 | 411 |
| Tanδ (60° C.) | 0.233 | 0.209 | 0.219 | 0.230 |
| After aging at 80° C. × 96 hours | | | | |
| 100% modulus (MPa) | 2.0 | 2.2 | 2.2 | 2.2 |
| 300% modulus (MPa) | 11.0 | 13.1 | 13.0 | 11.7 |

TABLE II-1-continued

|  | Comp. Ex. II-1 | Ex. II-1 | Ex. II-2 | Ex. II-3 |
| --- | --- | --- | --- | --- |
| TB (MPa) | 12.5 | 19.8 | 17.0 | 15.9 |
| EB (%) | 340 | 411 | 362 | 389 |
| Maintenance of physical properties after aging (aged/initial) | | | | |
| 100% modulus (%) | 123 | 113 | 108 | 108 |
| 300% modulus (%) | 122 | 102 | 108 | 101 |
| TB (%) | 78 | 82 | 80 | 81 |
| EB (%) | 81 | 95 | 88 | 95 |

Notes for Table II-1
*1Natural rubber (TSR-20)
*2Carbon black (Shoblack N335, Showa Cabot)
*3Zinc oxide (Ginrei R, Toho Zinc)
*4Stearic acid (Beads Stearic Acid YR, NOF Corporation)
*5Antioxidant (Santoflex 6PPD, Flexsys)
*6Vulcanization accelerator (Noccelar NS-P, Ouchi Shinko Chemical Industrial)
*7Sulfur (oil extended sulfur, Karuizawa Refinery)
*8Cyclic polysulfide (one synthesized in Preparation Example I-2 used)

As is clear from the results of Table II-1, Example II-1 uses only a cyclic polysulfide in an amount of 1 part by weight and exhibits excellent breaking characteristics and low tan δ both initially and after aging. Example II-2 is an example of use of a cyclic polysulfide and sulfur in a ratio of 1:1. Even if using sulfur together, similar effects are obtained. Example II-3 is an example of use of a cyclic polysulfide in an amount of 0.5 part by weight and exhibits excellent physical properties after aging.

Examples III-1 to III-4 and Comparative Examples III-1 to III-3

Preparation of Samples

In each of the formulations of Table III-1, the ingredients other than the vulcanization system were mixed in a 16-liter Banbury mixer for 5 minutes and were discharged when reaching 160±2° C. to obtain a master batch. This master batch was charged with the vulcanization system and moved by an open roll to obtain a rubber composition.

Next, the rubber composition obtained was vulcanized in a 15×15×0.2 cm mold at 160° C. for 30 minutes to prepare a vulcanized rubber sheet which was then measured for rubber properties by the following test methods. The results are shown in Table III-1.

Test Methods for Evaluation of Rubber Properties

Wet braking performance: A tire of size 195/65R15 using each compound as the tread was prepared, attached to a 2000 cc displacement vehicle, run over about six months on city streets for about 20,000 km, then measured for braking distance from an initial speed of 100 km on a test course of an asphalt surface sprinkled with water to a depth of 1 mm. The value of Comparative Example III-1 was indexed to as 100. The larger the number, the shorter the braking distance and the better.

TABLE III-1

|  | Comp. Ex. III-1 | Comp. Ex. III-2 | Ex. III-1 | Ex. III-2 | Ex. III-3 | Comp. Ex. III-3 | Ex. III-4 |
|---|---|---|---|---|---|---|---|
| Formulation (parts by weight) |  |  |  |  |  |  |  |
| Nipol 9526 | — | 120 | 120 | 120 | 120 | 120 | 120 |
| Nipol 1712 | 137.5 | — | — | — | — | — | — |
| Nipol 1220 | — | 20 | 20 | 20 | 20 | — | — |
| Dia I | 80 | 80 | 80 | 80 | 80 | 60 | 60 |
| Nipsil AQ | — | — | — | — | — | 20 | 20 |
| Si-69 | — | — | — | — | — | 1.0 | 1.0 |
| Santoflex 6PPD | 1 | 1 | 1 | 1 | 1 | 1 | 1 |
| Zinc oxide #3 | 3 | 3 | 3 | 3 | 3 | 3 | 3 |
| Stearic acid | 1 | 1 | 1 | 1 | 1 | 1 | 1 |
| Aromatic oil | 1.25 | 1.25 | 1.25 | 1.25 | 1.25 | 1.25 | 1.25 |
| Santocure CBS | 1.5 | 1.5 | 1.5 | 1.5 | 1.5 | 1.5 | 1.5 |
| Sulfur | 2.0 | 2.0 | — | — | 1.0 | 2.0 | — |
| Cyclic polysulfide III-1 | — | — | 3.0 | — | 1.5 | — | 3.0 |
| Cyclic polysulfide III-2 | — | — | — | 3.0 | — | — | — |
| Wet braking (index) | 100 | 103 | 110 | 109 | 109 | 104 | 112 |

Notes for Table III-1
Nipol 9526: Nippon Zeon styrene-butadiene copolymer rubber (styrene content: 35%, 50 phr, oil extended, Tg = −35° C.)
Nipol 1712: Nippon Zeon styrene-butadiene copolymer rubber (styrene content: 23.5%, 37.5 phr, oil extended, Tg = −51° C.)
Nipol 1220: Nippon Zeon polybutadiene rubber (non-oil extended, Tg = −100° C.)
DIA I: Mitsubishi Chemical carbon black ($N_2SA = 114$ m$^2$/g)
Nipsil AQ: Nippon Silica Industry wet type silica
Si-69: Degussa silane coupling agent
Santoflex 6PPD: Flexsys antioxidant
Sinc oxide #3: Seido Chemical Industry
Beads Stearic Acid: NOF Corporation stearic acid
Desolex No. 3: Showa Shell Oil process oil
Santocure CBS: Flexsys vulcanization accelerator
"Gold Flower" oil-treated sulfur powder: Tsurumi Chemical sulfur
Cyclic polysulfide III-1: Cyclic polysulfide having the formula (I) in which R = $(CH_2)_6$, x (average) = 4, and n = 1 to 5, synthesized according to the method of Example 3 of Japanese Unexamined Patent Publication (Kokai) No. 2002-293783.
Cyclic polysulfide III-2: Cyclic polysulfide having the formula (I) wherein R = $(CH_2)_2O(CH_2)O(CH_2)_2$, x (average) = 4 and n = 1 to 2, synthesized according to the method of Example 2 of Japanese Unexamined Patent Publication (Kokai) No. 2002-293783.

Examples III-5 to III-9 and Comparative Examples III-4 to III-7

In each of the formulations of Table III-2, the ingredients other than the vulcanization system (parts by weight) were mixed in a 16-liter Banbury mixer for 5 minutes then discharged, when reaching 150° C. to obtain a master batch. This master batch was charged with the vulcanization system and mixed by an open roll to obtain a rubber composition.

Next, the rubber composition was vulcanized in a 15×15×0.2 cm mold at 150° C. for 40 minutes to prepare a 2 mm thick vulcanized rubber sheet which was then measured for rubber properties by the following test methods. The results are shown in Table III-2.

Test Methods for Evaluation of Rubber Properties

Rate of change of M300: The rate of change of the 300% moduls before and after heat aging at 100° C. for 24 hours. If this rate of change is 10% or less, the grip is a stable good one.

Evaluation of grip: A 195/55R15 tire using each rubber composition as a tread was prepared and run a 4.41 km lap course. The grip performance was evaluated organoleptically in five rankings. The larger the value, the better the grip. Note that in Table III-2, each example exhibits a good rate of change of 300% modulus and grip.

TABLE III-2

|  | Comp. Ex. III-4 | Comp. Ex. III-5 | Comp. Ex. III-6 | Ex. III-5 | Ex. III-6 | Ex. III-7 | Ex. III-8 | Ex. III-9 | Comp. Ex. III-7 |
|---|---|---|---|---|---|---|---|---|---|
| Formulation (parts by weight) |  |  |  |  |  |  |  |  |  |
| SBR | 150 | 150 | 150 | 150 | 150 | 150 | 150 | 150 | 150 |
| Carbon SAF | 100 | 70 | 120 | 100 | 120 | 70 | 100 | 100 | 100 |
| Silica | — | — | — | — | — | 30 | — | — | — |
| Total amount of filler | 100 | 70 | 120 | 100 | 120 | 100 | 100 | 100 | 100 |
| Zinc white | 3 | 3 | 3 | 3 | 3 | 3 | 3 | 3 | 3 |
| Stearic acid | 2 | 2 | 2 | 2 | 2 | 2 | 2 | 2 | 2 |
| Antioxidant 6C | 2 | 2 | 2 | 2 | 2 | 2 | 2 | 2 | 2 |
| Si69 | — | — | — | — | — | 2.4 | — | — | — |

TABLE III-2-continued

|  | Comp. Ex. III-4 | Comp. Ex. III-5 | Comp. Ex. III-6 | Ex. III-5 | Ex. III-6 | Ex. III-7 | Ex. III-8 | Ex. III-9 | Comp. Ex. III-7 |
|---|---|---|---|---|---|---|---|---|---|
| Process oil | 30 | 0 | 50 | 30 | 50 | 30 | 30 | 30 | 30 |
| Accelerator CBS | 1.7 | 1.7 | 1.7 | 1.7 | 1.7 | 1.7 | 1.7 | 1.7 | 1.7 |
| Accelerator TOT-N | 2.0 | 2.0 | 2.0 | 2.0 | 2.0 | 2.0 | 2.0 | 2.0 | 2.0 |
| Sulfur | 1.6 | 0.8 | 1.6 | 0.8 | 0.8 | 0.8 | — | 1.4 | 1.5 |
| Cyclic polysulfide III-3 | — | 0.8 | — | 0.8 | 0.8 | 0.8 | 1.6 | 0.2 | 0.1 |
| Cyclic polysulfide + sulfur | 1.6 | 1.6 | 1.6 | 1.6 | 1.6 | 1.6 | 1.6 | 1.6 | 1.6 |
| Cyclic polysulfide ratio | 0.0 | 0.5 | 0.0 | 0.5 | 0.5 | 0.5 | 1.0 | 0.13 | 0.06 |
| Rate of change of M300 (%) | 30 | 2 | 42 | 4 | 7 | 3 | 3 | 6 | 11 |
| Evaluation of grip performance (index) | 3 | 2 | 4 | 4 | 5 | 4 | 4 | 4 | 4 |

Notes for Table III-2
SBR: Nippon Zeon Nipol 9526 (styrene content: 35%)
Carbon SAF: Mitsubishi Chemical Diablack A
Silica: Degussa Ultrasil 7000GR
Accelerator CBS: Ouchi Shinko Chemical Industrial Noccelar CZ-G
Accelerator TOT-N: Ouchi Shinko Chemical Industrial Noccelar TOT-N
Sulfur: Tsurumi Chemical
Cyclic polysulfide III-3: Same as above cyclic polysulfide III-1

Examples III-10 to III-14 and Comparative Examples III-8 to III-10

In each of the formulations shown in Table III-3, the ingredients other than the vulcanization system (parts by weight) were mixed by a 16-liter Banbury mixer for 5 minutes and discharged when reaching 160° C. to obtain a master batch. This master batch was charged with the vulcanization system and mixed by an open roll to obtain a rubber composition.

Next, the rubber composition was vulcanized in a 15×15× 0.2 cm mold at 160° C. for 30 minutes to prepare a 2 mm thick vulcanized rubber sheet which was then measured for rubber properties by the following test methods. The results are shown in Table III-3.

Test Methods for Evaluation of Rubber Properties
Ice braking performance: A tire of a size of 195/65R15 using each compound as the tread was prepared, attached to a 2000 cc displacement vehicle, run on over about six months on city streets for about 20,000 km, then measured for braking distance from an inital speed of 40 km on a test course of an icy road with an ice temperature of −5° C. The value of Comparative Example III-8 was indexed to as 100. The larger the value, the shorter the braking distance and the better.

TABLE III-3

|  | Comp. Ex. III-8 | Ex. III-10 | Ex. III-11 | Ex. III-12 | Comp. Ex. III-9 | Ex. III-13 | Comp. Ex. III-10 | Ex. III-14 |
|---|---|---|---|---|---|---|---|---|
| Formulation (parts by weight) | | | | | | | | |
| Natural rubber TSR20 | 50 | 50 | 50 | 50 | 50 | 50 | 50 | 50 |
| Nipol 1441 | 68.75 | 68.75 | 68.75 | 68.75 | 68.75 | 68.75 | 68.75 | 68.75 |
| Dia I | 50 | 50 | 50 | 50 | 40 | 40 | 40 | 40 |
| Nipsil AQ | — | — | — | — | 10 | 10 | — | — |
| Si-69 | — | — | — | — | 1.0 | 1.0 | — | — |
| Santoflex 6PPD | 1 | 1 | 1 | 1 | 1 | 1 | 1 | 1 |
| Zinc oxide #3 | 3 | 3 | 3 | 3 | 3 | 3 | 3 | 3 |
| Stearic acid | 1 | 1 | 1 | 1 | 1 | 1 | 1 | 1 |
| Aromatic oil | 11.25 | 11.25 | 11.25 | 11.25 | 11.25 | 11.25 | 11.25 | 11.25 |
| Santocure CBS | 1.5 | 1.5 | 1.5 | 1.5 | 1.5 | 1.5 | 1.5 | 1.5 |
| Matsumoto Microsphere F-100 | — | — | — | — | — | — | 3.0 | 3.0 |
| Sulfur | 2.0 | — | — | 1.0 | 2.0 | — | 2.0 | — |
| Cyclic polysulfide III-4 | — | 3.0 | — | 1.5 | — | 3.0 | — | 3.0 |
| Cyclic polysulfide III-5 | — | — | 3.0 | — | — | — | — | — |
| Ice braking (index) | 100 | 108 | 107 | 107 | 103 | 112 | 105 | 114 |

Notes for Table III-3
Natural rubber TSR20: SIR20 (Tg = −70° C.)
Nipol 1441: Nippon Zeon polybutadiene rubber (37.5 phr, oil extended, Tg = −101° C.)
DIA I: Mitsubishi Chemical carbon black ($N_2SA$ = 114 m$^2$/g)
Nipsil AQ: Nippon Silica Industry wet silica
Si-69: Degussa silane coupling agent
Santoflex 6PPD: Flexsys antioxidant
Zinc Oxide #3: Seido Chemical Industry
Beads Stearic Acid: NOF Corporation stearic acid
Desolex No. 3: Showa Shell Oil process oil
Santocure CBS: Flexsys vulcanization accelerator
"Gold Flower" oil-treated sulfur powder: Tsurumi Chemical sulfur
Cyclic polysulfide III-4: Same as above cyclic polysulfide III-1
Cyclic polysulfide III-5: Same as above cyclic polysulfide III-2

Examples III-15 to III-18 and Comparative
Examples III-11 to III-12

In each of the formulations shown in Table III-4, the ingredients other than the vulcanization system (parts by weight) were kneaded in a 16-liter Banbury mixer for 5 minutes and discharged when reaching 160° C. to obtain a master batch. This master batch was charged with the vulcanization system and mixed by an open roll to obtain a rubber composition.

Next, the rubber composition obtained was vulcanized in a 15×15×0.2 cm mold at 160° C. for 30 minutes to prepare a 2 mm thick vulcanized rubber sheet which was measured for rubber properties by the following test methods. The results are shown in Table III-4.

Test Methods for Evaluation of Rubber Properties

A tire having a two-layer structure tread having a thickness of the cap part of a maximum of 7 mm and a thickness of the base part of 2 mm was prepared in a size of 195/65R15 using each compound for the base part and used for the following test.

High speed durability: A JIS D 4230 JIS high speed durability test was conducted by a drum of a diameter of 1707 mm, then the speed was increased every 30 minutes by 10 km/hr. The test was continued until the tire broke. The results were indexed to the value of Comparative Example III-11 as 100. The larger the value, the longer the running distance and the better.

Rolling resistance: This was measured by an indoor drum type tire rolling resistance tester with a drum diameter of 1707 mm. The measurement conditions used were the JATMA Y/B2003 edition. The larger the value, the smaller the rolling resistance and the better.

Steering stability: A vehicle was run a slalom test course set with pylons at fixed intervals. The average speed was used to evaluate the steering stability. The value of Comparative Example III-11 was indexed to as 100. The larger the value, the better the steering stability.

TABLE III-4

|  | Comp. Ex. III-11 | Ex. III-15 | Ex. III-16 | Ex. III-17 | Comp. Ex. III-12 | Ex. III-18 |
|---|---|---|---|---|---|---|
| Formulation (parts by weight) | | | | | | |
| Natural rubber TSR20 | 70 | 70 | 70 | 70 | 70 | 70 |
| Nipol 1502 | 30 | 30 | 30 | 30 | 30 | 30 |
| Dia E | 55 | 55 | 55 | 55 | 55 | 55 |
| Santoflex 6PPD | 1 | 1 | 1 | 1 | 1 | 1 |
| Zinc oxide #3 | 3 | 3 | 3 | 3 | 3 | 3 |
| Stearic acid | 1 | 1 | 1 | 1 | 1 | 1 |
| Aromatic oil | 10 | 10 | 10 | 10 | 2 | 2 |
| Santocure NS | 1.5 | 1.5 | 1.5 | 1.5 | 1.5 | 1.5 |
| Sulfur | 2.4 | — | — | 1.2 | 2.4 | — |
| Cyclic polysulfide III-6 | — | 3.6 | — | 1.8 | — | 3.6 |
| Cyclic polysulfide III-7 | — | — | 3.6 | — | — | — |
| High speed durability test (index) | 100 | 107 | 108 | 107 | 93 | 100 |
| Rolling resistance (index) | 100 | 100 | 100 | 100 | 102 | 102 |
| Steering stability (index) | 100 | 100 | 100 | 100 | 103 | 104 |

Notes for Table III-4
Natural rubber TSR20: SIR20
Nipol 1502: Nippon Zeon styrene-butadiene copolymer rubber (styrene content: 23.5%)
Dia E: Mitsubishi Chemical carbon black ($N_2SA$ = 41 $m^2/g$)
Santoflex 6PPD: Flexsys antioxidant
Zinc Oxide #3: Seido Chemical Industry
Beads Stearic Acid: NOF Corporation stearic acid
Desolex No. 3: Showa Shell Oil process oil
Santocure NS: Flexsys vulcanization accelerator
"Gold Flower" oil-treated sulfur powder: Tsurumi Chemical sulfur
Cyclic polysulfide III-6: Same as above cyclic polysulfide III-1
Cyclic polysulfide III-7: Same as above cyclic polysulfide III-2

Examples IV-1 to IV-4 and Comparative
Examples IV-1 to IV-2

According to each of the formulations shown in Table IV-1, the ingredients other than the sulfur and cross-linking accelerator were mixed in a Banbury mixer for 5 minutes. Next, the mixed material obtained, sulfur, and cross-linking accelerator were mixed by an open roll to obtain a rubber composition. The rubber composition obtained was pressed at 160° C. for 20 minutes, cross-linked, and used for evaluation of the physical properties. The test methods are as follows.

Test Methods

Rupke JIS hardness Hs (20° C.): Durometer A hardness shown based on JIS K6253.

100% and 300% modulus: Measured based on JIS K6251.

Breaking strength TB (MPa): Measured based on JIS K6251.

Elongation at break EB (%): Measured based on JIS K6251.

tan δ (60° C.): Measured by a Toyo Seiki Seisakusho viscoelasticity spectrometer at an initial strain of 10%, amplitude of ±2%, and frequency of 20 Hz.

A tire having a size of 195/65R15 using each compound of the above Table for a high hardness reinforcement rubber of a height of 50 mm extending from the bead part to the tire sidewalls at the inside of the tire sidewalls was prepared and used for the following tests.

Load Durability Test

A JIS D4230, JATMA Y/B2003 edition load durability test was conducted by a drum of a diameter of 1707 mm, then the load was increased 20% every 5 hours. The test was continued until the tire broke. The results are shown indexed to Comparative Example IV-1 as 100. The larger the value, the longer the running distance and the better.

Rolling Resistance

This was measured by an indoor drum type tire rolling resistance tester having a drum diameter of 1707 mm. The measurement conditions used were the JATMA Y/B2003 edition. The larger the value, the smaller the rolling resistance and the better.

Steering Stability

A vehicle was run on a slalom test course set with pylons at fixed intervals. The average speed was used to evaluate the steering stability. The value of Comparative Example IV-1 was indexed to as 100. The larger the value, the better the steering stability.

As is clear from the results of Table IV-1, Examples IV-1 and IV-2 use only cyclic polysulfides, so are greatly improved in durability over Comparative Example IV-1 using only sulfur, while giving the same extent of rolling resistance and steering stability. Example IV-3 is an example of joint use of a cyclic polysulfide and sulfur and is greatly improved in durability over Comparative Example IV-1 using only sulfur while giving the same extent of rolling resistance and steering stability. Example IV-4 is an example of joint use of a cyclic polysulfide and heat curing resin and is improved in durability and steering stability compared with using the Comparative Examples using sulfur while giving the same extent of rolling resistance.

Reference Example V-1, Examples V-1 to V-4, and Comparative Example V-1

The following test was conducted to evaluate the physical properties of the rubber vulcanization agent of the present invention.

TABLE IV-1

|   | Comp. Ex. IV-1 | Ex. IV-1 | Ex. IV-2 | Ex. IV-3 | Comp. Ex. IV-2 | Ex. IV-4 |
|---|---|---|---|---|---|---|
| Formulation (parts by weight) | | | | | | |
| NR*1 | 70 | 70 | 70 | 70 | 70 | 70 |
| SBR*2 | 30 | 30 | 30 | 30 | 30 | 30 |
| Carbon black*3 | 85 | 85 | 85 | 85 | 70 | 70 |
| Antioxidant*4 | 1 | 1 | 1 | 1 | 1 | 1 |
| Zinc oxide*5 | 3 | 3 | 3 | 3 | 3 | 3 |
| Stearic acid*6 | 1 | 1 | 1 | 1 | 1 | 1 |
| Heat curing resin*7 | — | — | — | — | 10 | 10 |
| Aromatic oil*8 | 15 | 15 | 15 | 15 | 15 | 15 |
| Vulcanization accelerator*9 | 2.0 | 2.0 | 2.0 | 2.0 | 2.0 | 2.0 |
| Resin curing agent*10 | — | — | — | — | 0.5 | 0.5 |
| Sulfur*11 | 4.0 | — | — | 2.0 | 4.0 | — |
| Cyclic polysulfide IV-1*12 | — | 6.0 | — | 3.0 | — | 6.0 |
| Cyclic polysulfide IV-2*13 | — | — | 6.0 | — | — | — |
| Evaluation of tire | | | | | | |
| Load durability test (index) | 100 | 110 | 111 | 109 | 90 | 100 |
| Rolling resistance (index) | 100 | 100 | 100 | 100 | 101 | 101 |
| Steering stability (index) | 100 | 100 | 100 | 100 | 103 | 104 |
| Evaluation of physical properties | | | | | | |
| Rupke JIS hardness Hs (20° C.) | 75 | 75 | 75 | 75 | 85 | 85 |
| 100% modulus | 5.0 | 5.0 | 5.1 | 5.0 | 7.5 | 7.5 |
| Breaking strength TB | 17.3 | 18.9 | 18.8 | 18.3 | 14.2 | 15.9 |
| Elongation at break EM | 325 | 348 | 345 | 340 | 162 | 195 |
| tan δ (60° C.) | 0.273 | 0.270 | 0.272 | 0.270 | 0.243 | 0.240 |

Notes for Table IV-1
*1Natural rubber TSR20: SIR20
*2Nippon Zeon styrene-butadiene copolymer rubber Nipol 1502
*3Mitsubishi Chemical carbon black DIA HA ($N_2SA$ = 74 m$^2$/g)
*4Flexsys Santoflex 6PPD
*5Seido Chemical Industry Zinc Oxide #3
*6NOF Corporation Beads Stearic Acid
*7Sumitomo Dulles Sumilight Resin PR-12687 (cashew oil modified phenol resin)
*8Showa Shell Oil Desolex No. 3 (process oil)
*9Flexsys Santocure NS
*10Ouchi Shinko Chemical Industrial Noccelar H (resin curing agent hexamethylene tetramine)
*11Tsurumi Chemical "Gold Flower", oil-treated sulfur powder
*12Cyclic polysulfide of Preparation Example I-2 used
*13Cyclic polysulfide of Preparation Example III-2 used The formulations of the rubber (parts by weight) are shown in Table V-1.

TABLE V-1

|  | Ref. Ex. V-1 | Ex. V-1 | Comp. Ex. V-1 | Ex. V-2 | Ex. V-3 | Ex. V-4 |
|---|---|---|---|---|---|---|
| Formulation (parts by weight) | | | | | | |
| Butadiene rubber*[1] | 60 | 60 | 60 | 60 | 60 | 60 |
| Natural rubber*[2] | 40 | 40 | 40 | 40 | 40 | 40 |
| FEF grade carbon*[3] | 50 | 50 | — | 50 | 50 | 50 |
| HAF grade carbon*[4] | — | — | 45 | — | — | — |
| Zinc oxide*[5] | 5 | 5 | 5 | 5 | 5 | 5 |
| Stearic acid*[6] | 1 | 1 | 1 | 1 | 1 | 1 |
| Insoluble sulfur*[7] | 6 | 3 | 3 | — | — | 3 |
| Cyclic polysulfide V-1*[8] | — | 3 | 3 | 6 | 6 | — |
| Cyclic polysulfide V-2*[9] | — | — | — | — | — | 3 |
| Vulcanization accelerator*[10] | 2 | 2 | 2 | 2 | — | 2 |
| Vulcanization accelerator*[11] | — | — | — | — | 4 | — |
| Evaluation of physical properties | | | | | | |
| Initial (before aging) | | | | | | |
| 100% modulus (MPa) | 6.0 | 6.2 | 6.7 | 6.4 | 6.5 | 6.3 |
| TB (MPa) | 13.0 | 14.3 | 14.3 | 15.0 | 15.2 | 15.9 |
| EB (%) | 230 | 270 | 240 | 300 | 290 | 330 |
| tan δ (60° C.) | 0.11 | 0.10 | 0.16 | 0.09 | 0.07 | 0.08 |
| After aging at 80° C. × 96 hours | | | | | | |
| 100% modulus (MPa) | 7.6 | 6.7 | 7.4 | 6.6 | 6.6 | 6.4 |
| TB (MPa) | 14.0 | 14.7 | 15.0 | 15.5 | 15.3 | 16.1 |
| EB (%) | 180 | 250 | 200 | 280 | 280 | 330 |
| Maintenance of physical properties after aging (aged/initial) | | | | | | |
| 300% modulus (%) | 127 | 108 | 110 | 103 | 102 | 102 |
| TB (%) | 108 | 103 | 105 | 103 | 101 | 101 |
| EB (%) | 78 | 93 | 83 | 93 | 97 | 100 |
| De Mattia bending crack growth test | | | | | | |
| Times until sample breakage | 3000 | 7000 | 5000 | 11000 | 13000 | 16000 |
| Rubber heat buildup | | | | | | |
| Sample temperature (° C.) | 38 | 37 | 46 | 35 | 34 | 34 |

Notes for Table V-1
*[1]Nipol BR1220 (Tg = −100° C.) (Nippon Zeon)
*[2]TSR 20
*[3]Diablack E (Mitsubishi Chemical, $N_2SA = 33\ m^2/g$)
*[4]Shoblack N339 (Showa Cabot, $N_2SA = 90\ m^2/g$)
*[5]Zinc White #3 (Seido Chemical Industry)
*[6]Beads Stearic Acid (Kao)
*[7]Crystex HSOT20 (Flexsys)
*[8]Above synthetic cyclic polysulfide I-2 used
*[9]Above synthetic cyclic polysulfide III-2 used
*[10]Noccelar NS-F (Ouchi Shinko Chemical Industrial, sulfenamide based)
*[11]Noccelar TOT-N (Ouchi Shinko Chemical Industrial, thiuram based)

A rubber composition having each formulation shown in Table V-1 (parts by weight) was mixed by an 8-inch open roll, then vulcanized under the vulcanization conditions of 160° C. and 20 minutes. The results are shown in Table V-1. The test methods are as follows.

100% modulus: Measured based on JIS K6251 (JIS No. 3 Dumbbell Shape).

Breaking strength TB: Measured based on JIS K6251 (JIS No. 3 Dumbbell Shape).

Elongation at break EB: Measured based on JIS K6251 (JIS No. 3 Dumbbell Shape).

De Mattia flex crack growth test: Measured according to JIS K6260 by clamping vulcanized rubber test piece notched in advance at a distance of 65 mm, bent at a stroke of 20 mm and a bending speed of 300 rpm, and measured for length of growth of the crack every 1000 bends. The number of bends when the crack reached the two ends of the sample are shown in the Table. The greater the number of bends, the better the resistance to crack growth.

Rubber heat buildup: The heat buildup of the side reinforcement rubber at the time of run flat operation was evaluated by the following test.

A vulcanized rubber sheet having a thickness of 5 mm and a width of 25 mm was attached to a de Mattia flex crack growth tester and bent by a stroke of 40 mm and a bending speed of 300 rpm. The surface temperature of the center of the sample after 30 minutes was measured by a noncontact type thermometer. The higher the temperature, the higher the heat buildup of the rubber due to the bending shown.

The Reference Example is evaluated based on this rubber in the example of the conventional side reinforcement rubber. Example V-1 shows the compound V-1 replaced about half by sulfur and is improved in heat aging resistance and improved in crack growth resistance. Comparative Example V-1 shows the case where the carbon is outside the prescribed scope and the heat buildup due to the bending is large. Example V-2 shows the case where the compound 1 is replaced entirely with sulfur and is further improved in heat aging resistance and is improved in crack growth resistance. Example V-3 shows the example of use of a thiuram-based vulcanization accelerator and is improved in heat aging resistance. Example V-4 shows the case of use of the compound V-2 and is further improved in heat aging resistance and greatly improved in crack growth.

Comparative Example, Examples VI-1 to VI-5, and Comparative Example VI-1

The following test was conducted for evaluating the physical properties of the rubber composition of the present invention.

The formulation of the rubber composition (parts by weight) is as shown in Table VI-1.

TABLE VI-1

|  | Conv. Ex. | Ex. VI-1 | Ex. VI-2 | Comp. Ex. VI-1 | Ex. VI-3 | Ex. VI-4 | Ex. VI-5 |
|---|---|---|---|---|---|---|---|
| Formulation (parts by weight) | | | | | | | |
| Natural rubber*[1] | 100 | 100 | 100 | 100 | 100 | 100 | 100 |
| Carbon black*[2] | 60 | 60 | 60 | 60 | 60 | 60 | 60 |
| Zinc oxide*[3] | 5 | 5 | 5 | 5 | 5 | 5 | 5 |
| Stearic acid*[4] | 1 | 1 | 1 | 1 | 1 | 1 | 1 |
| Antioxidant*[5] | 1 | 1 | 1 | 1 | 1 | 1 | 1 |
| Cobalt naphthenate*[6] | — | — | — | — | — | — | 5 |
| Alkylphenol resin*[7] | — | — | — | — | — | — | 4 |
| Sulfur*[8] | 4 | — | 3 | 5 | 2 | 1 | 1 |
| Cyclic polysulfide VI-1*[9] | — | 2 | 3 | 2 | 2 | 3 | 3 |
| Vulcanization accelerator*[10] | 1 | 1 | 1 | 1 | — | — | — |
| Vulcanization accelerator*[11] | — | — | — | — | 3 | — | — |
| Vulcanization accelerator*[12] | — | — | — | — | — | 4 | 4 |
| Initial (heat aging characteristics) | | | | | | | |
| 100% modulus (MPa) | 5.2 | 4.4 | 6.0 | 7.6 | 5.8 | 6.1 | 6.3 |
| TB (MPa) | 18.0 | 20.3 | 22.0 | 19.8 | 24.0 | 23.5 | 22.3 |
| EB (%) | 260 | 320 | 280 | 230 | 340 | 320 | 300 |
| Heat aging after 80° C. × 96 hours | | | | | | | |
| 100% modulus (MPa) | 6.8 | 4.8 | 6.4 | 8.5 | 6.0 | 6.3 | 6.5 |
| TB (MPa) | 16.8 | 19.5 | 22.8 | 15.6 | 23.5 | 23.1 | 21.9 |
| EB (%) | 210 | 310 | 250 | 170 | 330 | 300 | 280 |
| Maintenance of physical properties after aging (aged/initial) | | | | | | | |
| 100% modulus (%) | 131 | 109 | 107 | 112 | 103 | 103 | 103 |
| TB (MPa) | 93 | 96 | 104 | 79 | 98 | 98 | 98 |
| EB (%) | 81 | 97 | 89 | 74 | 97 | 94 | 93 |
| Run flat durability test | | | | | | | |
| Method of bonding with shell | Adhesive[13] | Adhesive*[13] | Adhesive*[13] | Adhesive*[13] | Adhesive*[13] | Adhesive*[13] | No adhesive |
| Index value*[1] | 100 | 105 | 125 | 96 | 130 | 144 | 136 |

*[1]Indexed to value of conventional example as 100 (the larger the value, the better the durability)
Notes for Table VI-1
*[1]TSR20
*[2]HTC100 (NSC Carbon)
*[3]Zinc White #3 (Seido Chemical Industry)
*[4]Beads Stearic Acid (Kao)
*[5]Nocrac 6C (Ouchi Shinko Chemical Industrial)
*[6]Cobalt naphthenate (CO content 10%) (Dainippon Ink & Chemical)
*[7]Hitanol 2501Y (Hitachi Chemical)
*[8]Oil extended sulfur (Karuizawa Refinery)
*[9]Cyclic polysulfide synthesized in Production Example I-2
*[10]Noccelar DM (thiazole based) (Ouchi Shinko Chemical Industrial)
*[11]Noccelar TOT-N (thiuram based) (Ouchi Shinko Chemical Industrial)
*[12]Noccelar NS-F (sulfenamide based) (Ouchi Shinko Chemical Industrial)
*[13]Chemlock 205 (Lord)

In the rubber composition having each formulation shown in Table VI-1 (parts by weight), the ingredients excluding the vulcanization agent were mixed in a 16-liter tangential type mixer, then mixed with the vulcanization agent by an 8-inch open roll, then vulcanized under the vulcanization conditions of 160° C. and 20 minutes to vulcanize the rubber. The results are shown in Table VI-1. The test methods are as follows.

100% modulus: Measured according to JIS K6251 (JIS No. 3 Dumbbell Shape)

Breaking strength TB: Measured according to JIS K6251 (JIS No. 3 Dumbbell Shape)

Elongation at break EB: Measured according to JIS K6251 (JIS No. 3 Dumbbell Shape)

Run flat durability test: A core ring was prepared using the formulation of each of the Comparative Examples and examples for elastic rings and assembled inside a 16×6.5JJ rim 205/55R16 tire. The tire was attached to the right front wheel of a passenger car with a displacement of 2.5 liters, set to an air pressure of 0 kPa, and run over an elliptical course at a speed of 90 km/h counterclockwise. The distance until the driver felt an abnormality and stopped driving was measured. The results are shown indexed to the value of Comparative Example VI-1 as 100. The larger the value, the better the durability.

The conventional example shows a conventional typical elastic ring formulation. Other examples were evaluated based on the physical properties of the composition and the run flat distance. Comparative Example VI-1 is an example where the amount of vulcanization agent is too small and has too low a modulus of rubber and low run flat distance. Example VI-1 is an example of suitable amount of blending of a vulcanization agent and had run flat performance even with a modulus lower than the conventional example. Example VI-2 is an example using both sulfur and cyclic polysulfide in a suitable ratio. The rubber properties become better and the run flat performance is improved. Comparative Example VI-2 shows the case where the ratio of the sulfur and cyclic polysulfide is more than 2 and the aging resistance of the rubber deteriorates and the run flat performance deteriorates. Example VI-3 shows the case of using a thiuram-based accelerator and is improved in run flat performance. Example VI-4 shows the case of raising the accelerator ratio by using a sulfenamide-based accelerator and is further improved in run flat performance. Example VI-5 shows an example of blending an organic acid cobalt and alkylphenol resin into an elastic ring rubber composition and enabling direct bonding to the shell without an adhesive.

Examples VII-1 to 4 and Comparative Example VII-1

The following tests were conducted to evaluate the physical properties of the rubber vulcanization agent of the present invention.

The formulations into the rubber (parts by weight) were as shown in Table VII-I.

TABLE VII-1

| | Comp. Ex. | Example | | | | |
|---|---|---|---|---|---|---|
| | VII-1 | VII-1 | VII-2 | VII-3 | VII-4 | VII-5 |
| Formation (parts by weight) | | | | | | |
| Natural rubber*1 | 20 | 20 | 20 | 20 | 20 | 20 |
| Brominated butyl rubber*2 | 80 | 80 | 80 | 80 | 80 | 80 |

TABLE VII-1-continued

| | Comp. Ex. | Example | | | | |
|---|---|---|---|---|---|---|
| | VII-1 | VII-1 | VII-2 | VII-3 | VII-4 | VII-5 |
| Carbon black*3 | 60 | 60 | 60 | 60 | 60 | 60 |
| Zinc oxid*4 | 3 | 3 | 3 | 3 | 3 | 3 |
| Stearic acid*5 | 1 | 1 | 1 | 1 | 1 | 1 |
| Aromatic petroleum resin*6 | 10 | 10 | 10 | 10 | 10 | 10 |
| Aromatic oil*7 | 5 | 5 | 5 | 5 | 5 | 5 |
| Sulfur*8 | 0.5 | 0.25 | — | — | — | — |
| Cyclic polysulfide VII-1*9 | — | 0.3 | 0.7 | — | 0.7 | 0.7 |
| Cyclic polysulfide VII-2*10 | — | — | — | 0.7 | — | — |
| Vulcanization accelerator*11 | 1 | 1 | 1 | 1 | — | — |
| Vulcanization accelerator*12 | — | — | — | — | 2 | — |
| Vulcanization accelerator*13 | — | — | — | — | — | 2 |
| Initial (heat aging) | | | | | | |
| 300% modulus (MPa) | 4.5 | 4.6 | 4.8 | 4.4 | 5 | 4.9 |
| TB (MPa) | 8.0 | 8.5 | 9.1 | 9.3 | 9.8 | 10.1 |
| EB (%) | 580 | 610 | 650 | 680 | 690 | 680 |
| After 80° C. × 96 hours aging | | | | | | |
| 300% modulus (MPa) | 4.7 | 4.8 | 4.9 | 4.4 | 5.1 | 5.1 |
| TB (MPa) | 7.6 | 8.6 | 9.2 | 9.3 | 9.7 | 9.9 |
| EB (%) | 540 | 600 | 650 | 670 | 680 | 670 |
| Maintenance of physical properties after aging (aged/initial) | | | | | | |
| 300% modulus (%) | 104 | 103 | 102 | 100 | 102 | 103 |
| TB (%) | 95 | 101 | 101 | 100 | 99 | 98 |
| EB (%) | 93 | 98 | 100 | 99 | 99 | 99 |
| Embrittlement temperature (° C.) | −38.8 | −40.0 | −41.8 | −42.3 | −41.6 | −42.0 |

Notes for Table VII-1
*1TSR20
*2Bromobutyl 2255 (Exxon Mobile Chemical)
*3Diablack E (Mitsubishi Chemical)
*4Zinc White #3 (Seido Chemical Industry)
*5Beads Stearic Acid (Kao)
*6FR-120 (Fujikosan)
*7Extract No. 4S (Showa Shell Oil)
*85% oil extended sulfur (Karuizawa Refinery)
*9Cyclic polysulfide synthesized in Preparation Example I-2
*10Cyclic polysulfide synthesized in Preparation Example III-2
*11Noccelar DM (Ouchi Shinko Chemical Industrial)
*12Noccelar TOT-N (Ouchi Shinko Chemical Industrial)
*13Noccelar NS-F (Ouchi Shinko Chemical Industrial)

The rubber composition having each of the formulations shown in Table VII-1 (parts by weight) was mixed by an 8-inch open roll, then the rubber was vulcanized under vulcanization conditions of 160° C. and 20 minutes. The results are shown in Table VII-1. The test methods are as follows.

300% modulus: According to JIS K6251 (No. 3 Dumbbell)

Breaking strength TB: According to JIS K6251 (No. 3 Dumbbell)

Elongation at break EB: According to JIS K6251 (No. 3 Dumbbell)

Impact brittleness temperature: According to JIS K6261, rubber brittleness temperature measured.

Note that Comparative Example VII-1 is an inner liner formulation rubber of a conventional sulfur formulation, Example VII-1 is an example of replacement of about half of the cyclic polysulfide VII-1 and is improved in elongation and rate of maintenance after heat aging. Example VII-2 is an example of sulfur replaced by the cyclic polysulfide VII-1 and is further improved in elongation and also improved in maintenance after heat aging. Example VII-3 is an example of use of cyclic polysulfide VII-2 with a different skeleton and is further improved in breaking physical properties. Example VII-4 shows the case using a thiuram-based vulcanization accelerator and is improved in modulus and breaking characteristics. Example VII-5 shows the case using a sulfenamide-based vulcanization accelerator and is improved in the modulus and breaking characteristics.

Preparation Example VIII-1 (Production of Vulcanization Agent VIII-3)

A 30% by weight aqueous sodium tetrasulfide solution in an amount of 89.8 g (0.15 mole) was diluted by 100 g of water, dropped with 25.9 g (0.15 mole) of 1,2-bis(2-chloroethoxy) methane at 90° C. over 2 hours, and was allowed to react at that temperature for a further 3 hours. After the reaction was ended, the aqueous insolubles were rinsed, then dried under reduced pressure at 100° C. for 2 hours to thereby obtain a cyclic polysulfide of formula (I) wherein R=—$CH_2CH_2OCH_2OCH_2CH_2$—, x (average)=4 and n=1 to 5 (vulcanization agent 3) in an amount of 33.2 g (yield 96%). The cyclic polysulfide obtained had a number average molecular weight of 600. Its NMR data is as follows.

$^1$H-NMR *(chloroform-di) δ: 2.9 to 3.3(4H,$CH_2$S), 3.7 to 4.0(4H,$CH_2$O), 4.8(2H,$OCH_2$O).

Examples VIII-1 to VIII-3 and Comparative Example VIII-1

The rubber composition having each of the formulations shown in Table VIII-1 (parts by weight) was mixed by an 8-inch open roll, then vulcanized under vulcanization conditions of 170° C. and 10 minutes. The results are shown in Table VIII-1. The test methods are as follows.

100% modulus: Measured according to JIS K6251 (JIS No. 3 dumbbell, test speed 500 mm/min).

Breaking strength (TB): Measured according to JIS K6251 (JIS No. 3 dumbbell, test speed 500 mm/min).

Elongation at break (EB): Measured according to JIS K6251 (JIS No. 3 dumbbell, test speed 500 mm/min).

TABLE VIII-1

|  | Comp. Ex. VIII-1 | Ex. VIII-1 | Ex. VIII-2 | Ex. VIII-3 |
|---|---|---|---|---|
| Formulation (parts by weight) | | | | |
| Natural rubber*$^1$ (RSS#3) | 100.0 | 100.0 | 100.0 | 100.0 |
| Carbon black*$^2$ (N326) | 60.0 | 60.0 | 60.0 | 60.0 |
| Zinc white*$^3$ | 10.0 | 10.0 | 10.0 | 10.0 |
| Stearic acid*$^4$ | 0.5 | 0.5 | 0.5 | 0.5 |
| Antioxidant*$^5$ (6PPD) | 2 | 2 | 2 | 2 |
| Organic acid cobalt*$^7$ (as CO) | 0.2 | 0.2 | 0.2 | 0.2 |
| Sulfur*$^8$ | 8.0 | 4.0 | 4.0 | 4.0 |
| Vulcanization agent VIII-1*$^9$ | — | 4.0 | — | — |
| Vulcanization agent VIII-2*$^{10}$ | — | — | 3.6 | — |
| Vulcanization agent VIII-3*$^{11}$ | — | — | — | 4.4 |
| Vulcanization accelerator*$^{12}$ (DZ) | 0.5 | 0.5 | 0.5 | 0.5 |
| Evaluation of physical properties Initial (before aging) | | | | |
| 100% modulus (MPa) | 3.5 | 3.9 | 3.6 | 4.0 |
| TB (MPa) | 23.4 | 23.5 | 21.7 | 23.4 |
| EB (%) | 490 | 460 | 460 | 430 |

TABLE VIII-1-continued

|  | Comp. Ex. VIII-1 | Ex. VIII-1 | Ex. VIII-2 | Ex. VIII-3 |
|---|---|---|---|---|
| After 80° C. × 96 hours heat aging | | | | |
| 100% modulus (MPa) | 7.5 | 6.8 | 6.3 | 7.2 |
| TB (MPa) | 17.9 | 19.5 | 19.3 | 20.e5 |
| EB (%) | 230 | 280 | 290 | 270 |
| Maintenance of physical properties after aging (aged/initial) | | | | |
| 100% modulus (%) | +114 | +75 | +76 | +77 |
| TB (%) | −24 | −17 | −11 | −12 |
| EB (%) | −53 | −49 | −39 | −37 |

Notes for Table VIII-1
*$^1$RSS#3
*$^2$Mitsubishi Chemical Diablack E
*$^3$Seido Chemical Industry Zinc Oxide #3
*$^4$NOF Corporation Beads Stearic Acid
*$^5$Flexsys Santoflex PPD
*$^7$Rhodia Manobond C22.5
*$^8$Akzo Nobel Crystex HS
*$^9$One synthesized in Preparation Example III-1 used
*$^{10}$One synthesized in Preparation Example I-2 used
*$^{11}$One synthesized in Preparation Example VIII-1 used
*$^{12}$Ouchi Shinko Chemical Industrial Noccelar DZ-G Comparative Example VIII-1 is an example of a conventional belt coat compound. This example is used as the reference for evaluation of the rubber compositions of the present invention. Examples VIII-1 to VIII-3 show cases with sulfur replaced with cyclic polysulfides (vulcanization agents VIII-1 to VIII-3) and are improved in initial 100% modulus and physical properties after aging.

Standard Example IX-1

A mixed solvent of a 30% aqueous sodium polysulfide ($Na_2S_4$) solution in an amount of 119.7 g (0.2 mol) in 50 g of toluene was charged with 0.64 g (1 mol %) of tetrabutyl ammonium bromide and dropped with 34.6 g (0.2 mol) of dichloroethyl formal dissolved in 30 g of toluene at 90° C. over 30 minutes and a reaction caused for 5 hours. After the reaction, the organic phase was separated and concentrated under reduced pressure at 90° C. to obtain the cyclic polysulfide IX-1 in an amount of 45.0 g (yield 97.8%). The cyclic polysulfide obtained was confirmed by GPC, whereupon the number average molecular weight was 570.

Example IX-1

A mixed solvent of 1,2-dichloroethane in an amount of 1.98 g (0.02 mol) and a 30% aqueous sodium polysulfide ($Na_2S_4$) solution in an amount of 1197 g (2 mol) in 500 g of toluene was charged with 0.64 g (0.1 mol %) of tetrabutyl ammonium bromide at 50° C. for 2 hours. Next, 311.0 g (1.8 mol) of dichloroethyl formal was dissolved in 300 g of toluene, then the reaction temperature of the mixture was increased to 90° C., dropped over 1 hour, and reacted over 5 hours. After the reaction, the organic phase was separated and concentrated under reduced pressure at 90° C. to obtain cyclic polysulfide IX-2 in an amount of 405 g (yield 96.9%). The cyclic polysulfide obtained was confirmed by GPC, whereupon the number average molecular weight was 530.

Example IX-2

A mixed solvent of 1,2-dichloroethane in an amount of 1.98 g (0.02 mol) and a 30% aqueous sodium polysulfide ($Na_2S_4$) solution in an amount of 119.7 g (0.2 mol) in 50 g of toluene was charged with 0.64 g (1 mol %) of tetrabutyl ammonium bromide and reacted at 50° C. for 2 hours. Next, 31.1 g (0.18 mol) of dichloroethyl formal was dissolved in 30 g of toluene, then the reaction temperature of the mixture was increased to 90° C., dropped over 30 minutes, then further reacted for 5 hours. After the reaction, the organic phase was separated and concentrated under reduced pressure at 90° C. to obtain cyclic polysulfide IX-3 in an amount of 43.8 g (yield 98%). The cyclic polysulfide obtained was confirmed by GPC, whereupon the number average molecular weight was 630.

TABLE IX-1

|  | Viscosity (80° C.) (Pa · s) |
|---|---|
| Cyclic polysulfide IX-1 | 272 |
| Cyclic polysulfide IX-2 | 70 |
| Cyclic polysulfide IX-3 | 8.2 |

Standard Example IX-2, Examples IX-3 to IX-4, and Comparative Example IX-1

Preparation of Sample

In each of the formulations shown in Table IX-2, the ingredients other than the vulcanization accelerator and sulfur were mixed in an internal mixer to obtain a master batch. This master batch had the vulcanization accelerator and sulfur mixed into it by an open roll to obtain a rubber composition.

Next, the rubber composition obtained was vulcanized in a 15×15×0.2 cm mold at 150° C. for 30 minutes to prepare a vulcanized rubber sheet, which was then measured for the physical properties of the vulcanized rubber by the following test methods. The results are shown in Table IX-2.

Test Methods for Evaluation of Rubber Properties

100% and 300% modulus (MPa): Measured according to JIS K6251

Breaking strength TB (MPa): Measured according to JIS K6251

Elongation at break EB (%): Measured according to JIS K6251

TABLE IX-2

|  | Standard Example IX-2 | Comparative Example IX-1 | Example IX-3 | Example IX-4 |
|---|---|---|---|---|
| Formulation (parts by weight) | | | | |
| Natural rubber[*1] | 100 | 100 | 100 | 100 |
| Carbon black[*2] | 50 | 50 | 50 | 50 |
| Zinc oxide[*3] | 3 | 3 | 3 | 3 |
| Stearic acid[*4] | 2 | 2 | 2 | 2 |
| Antioxidant[*5] | 1 | 1 | 1 | 1 |
| Vulcanization accelerator[*6] | 1 | 1 | 1 | 1 |
| Sulfur[*7] | — | 1 | — | — |

TABLE IX-2-continued

|  | Standard Example IX-2 | Comparative Example IX-1 | Example IX-3 | Example IX-4 |
|---|---|---|---|---|
| Cyclic polysulfide IX-1[*8] | 6 | — | — | — |
| Cyclic polysulfide IX-2[*9] | — | — | 6 | — |
| Cyclic polysulfide IX-3[*10] | — | — | — | 6 |
| Evaluation of physical properties | | | | |
| 100% modulus (MPa) | 3.1 | 3.0 | 3.2 | 3.5 |
| 300% modulus (MPa) | 16.9 | 17.1 | 16.8 | 17.9 |
| TB (MPa) | 28.9 | 29.5 | 29.1 | 28.1 |
| EB (%) | 485 | 493 | 512 | 485 |

Notes for Table IX-2
[*1]RSS#3
[*2]Tokai Carbon Seast N
[*3]Seido Chemical Industry Zinc White 3
[*4]Kao Beads Stearic Acid
[*5]Ouchi Shinko Chemical Industrial Nocrac 6C
[*6]Ouchi Shinko Chemical Industrial Noccelar NS-F
[*7]Karuizawa Refinery oil extended sulfur
[*8]See Standard Example IX-1
[*9]See Example IX-1
[*10]See Example IX-2

According to the present invention, as explained above, by using two or more types of dihalogen compounds for a condensation reaction with the metal polysulfide, when blending, into the rubber composition, a vulcanization agent, it is possible to obtain a rubber composition excellent in heat aging resistance, without exceeding the increase in the viscosity of the rubber composition and, without decreasing the vulcanization efficiency, and therefore, this is useful for a pneumatic tire cap, belt, hose, conveyor belt, etc.

INDUSTRIAL APPLICABILITY

The rubber composition according to the first aspect of the present invention, in addition to the heat aging resistance, can suppress the heat buildup by making the average number of sulfur of the cyclic polysulfide having the formula (I) more than 4 to 6, preferably about 4.5 to 5, so, for example, can be suitably used for a pneumatic tire cap, belt, undertread, side, carcass coat, bead filler, rim cushion, inner liner, rubber tube, hose, conveyor belt, rubber vibration absorber, rubber roll, air type fender, shoe soles, rubber packing, vibration damper, sponge rubber product, rubber window seal, etc.

The rubber composition according to the second aspect of the present invention has good breaking characteristics before and after aging and a low tan δ, so for example is useful as a pneumatic tire cap tread, belt coat, sidewall, carcass coat, undertread, bead filler, rim cushion, etc.

The rubber composition according to the third aspect of the present invention can improve the grip performance, breaking strength, grip sustainability, durability, and steering stability, so, for example, is useful as a cap part or base part of the tread of a pneumatic tire.

The rubber composition according to the fourth aspect of the present invention has a high hardness, high tensile strength and elongation at break, and good heat buildup (tan δ), so, for example, is useful as a bead filler of a pneumatic tire.

The rubber composition according to the fifth aspect of the present invention is excellent in the fatigue resistance (crack growth resistance) required for the side reinforcement rubber of a run flat tire, so, for example, is useful as side reinforcement rubber or bead filler inserted in the crescent shaped cross-section at the inside of the sides of the pneumatic tire having a run flat performance.

The rubber composition according to the sixth aspect of the present invention is excellent in run flat performance and heat aging resistance, so for example is useful as an elastic ring of a run flat tire core ring.

The rubber composition according to the seventh aspect of the present invention is excellent in breaking characteristics and low temperature characteristics, so, for example, is useful as a pneumatic tire inner liner layer, cap tread, side tread, a tube tire inner tube, air type fender, rubber vibration absorber, multilayer rubber vibration absorber, winter shoe sole, automobile engine mount, rubber bushing, hose, marine hose, vulcanization bladder, cable, shock absorber, noise absorber, etc.

The rubber composition according to the eighth aspect of the present invention has a higher rigidity than conventional compounds and further is excellent in heat aging resistance, so, for example, is useful as a belt coat compound for a pneumatic tire.

LIST OF REFERENCES

1 . . . run flat core ring
2 . . . pneumatic tire
3 . . . cavity
4 . . . ring-shaped metal shell
5 . . . elastic ring
6 . . . rim

The invention claimed is:

1. A rubber composition for ice and snow roads, comprising 100 parts by weight of a sulfur-vulcanizable rubber (A) and, as a vulcanization agent, 0.1 to 30 parts by weight of a cyclic polysulfide (B) having the formula (I):

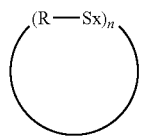

(I)

wherein R is a substituted or unsubstituted $C_2$ to $C_{20}$ alkylene group, substituted or unsubstituted $C_2$ to $C_{20}$ oxyalkylene group or alkylene group having an aromatic ring, n is an integer of 1 to 20 and x is an average number of 2 to 6; and (C) a heat expandable thermoplastic resin or heat expandable graphite, wherein the sulfur-vulcanizable rubber (A) is a sulfur-vulcanizable rubber mainly composed of natural rubber and/or polybutadiene rubber, the blended amount of the cyclic polysulfide having the formula (I) is 0.1 to 10 parts by weight and wherein the composition further contains 10 to 100 parts by weight of a softening agent having a weight average molecular weight, converted to polystyrene, of 100,000 or less.

2. A rubber composition as claimed in claim 1, wherein the sulfur-vulcanizable rubber (A) has an average glass transition temperature (Tg) of −100° C. to −50° C.

3. A rubber composition as claimed in claim 1 further comprising silica and/or carbon black having a nitrogen specific surface area ($N_2SA$) of 85 $m^2/g$ to less than 150 $m^2/g$ in a total amount of 40 to 100 parts by weight, based upon 100 parts by weight of the sulfur-vulcanizable rubber (A).

4. A rubber composition as claimed in claim 1, wherein the cyclic polysulfide is obtained by a reaction between a dihalogen compound having a formula: X—R—X, wherein X independently indicate a halogen atom, R indicates a substituted or unsubstituted $C_2$ to $C_{20}$ alkylene group or oxyalkylene group or an alkylene group including an aromatic ring and an alkali metal polysulfide having a formula $M-S_x-M$, wherein M is an alkali metal, x is an integer of 2 to 6, in a hydrophilic solvent or a non-compatible mixed solvent of hydrophilic/lyophilic solvents as a two-phase system reaction.

5. The rubber composition as claimed in claim 1, wherein the amount of the heat expandable thermoplastic resin or heat expandable graphite is about 1 to about 15 parts by weight per 100 parts by weight of the rubber.

6. The rubber composition as claimed in claim 1, wherein the amount of the heat expandable thermoplastic resin is about 2 to about 10 parts by weight per 100 parts by weight of the rubber.

7. The rubber composition as claimed in claim 1, wherein the amount of the heat expandable graphite is about 2 to about 8 parts by weight per 100 parts by weight of the rubber.

8. The rubber composition as claimed in claim 1, wherein the particle size of the heat expandable thermoplastic resin is 5 to 300 μm before expansion.

9. The rubber composition as claimed in claim 1, wherein the particle size of the heat expandable thermoplastic resin is 10 to 200 μm before expansion.

10. The rubber composition as claimed in claim 1, wherein the particle size of the heat expandable graphite is 30 to 600 μm before expansion.

11. The rubber composition as claimed in claim 1, wherein the particle size of the heat expandable graphite is 100 to 350 μm before expansion.

* * * * *